United States Patent
De Cicco et al.

(10) Patent No.: US 11,369,346 B2
(45) Date of Patent: Jun. 28, 2022

(54) DEVICES AND METHODS FOR INTRAHEPATIC SHUNTS

(71) Applicant: VOLCANO CORPORATION, San Diego, CA (US)

(72) Inventors: Dino De Cicco, San Diego, CA (US); Jeremy Stigall, San Diego, CA (US); John Unser, Temecula, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 895 days.

(21) Appl. No.: 14/800,283

(22) Filed: Jul. 15, 2015

(65) Prior Publication Data

US 2016/0015422 A1 Jan. 21, 2016

Related U.S. Application Data

(60) Provisional application No. 62/024,520, filed on Jul. 15, 2014.

(51) Int. Cl.
*A61B 17/34* (2006.01)
*A61B 8/08* (2006.01)
(Continued)

(52) U.S. Cl.
CPC ............ *A61B 8/461* (2013.01); *A61B 8/0841* (2013.01); *A61B 8/0891* (2013.01); *A61B 8/12* (2013.01);
(Continued)

(58) Field of Classification Search
CPC ........ A61B 8/6853; A61B 2017/22054; A61B 8/461; A61B 8/0841; A61B 8/12;
(Continued)

(56) References Cited

U.S. PATENT DOCUMENTS 4,274,423 A * 6/1981 Mizuno ................ A61B 5/0215
600/488
4,794,931 A 1/1989 Yock
(Continued)

FOREIGN PATENT DOCUMENTS

EP 976363 A2 2/2000
WO 1999048545 A1 9/1999
(Continued)

OTHER PUBLICATIONS

Vasconcelos-Filho et al. "Measurements between the hepatic veins and portal venous system, in human cirrhotic liver: a cast study" Surgical and Radiologic Anatomy. vol. 40, pp. 395-400 (2018) (Year: 2018).*
(Continued)

*Primary Examiner* — Colin T. Sakamoto

(57) ABSTRACT

The invention provides methods and devices for treating liver cirrhosis or portal hypertension by creating an intrahepatic shunt, or new passage, from a portal vein of a patient to a hepatic vein using a device with intravascular imaging capabilities and pressure sensing capabilities or positioning mechanisms. The integration of intravascular imaging aids in the precise placement of the shunt and pressure measurement may verify successful shunt creation. An apparatus may include a catheter with an extended body for insertion into a hepatic vein of a patient, an intravascular imaging device and a needle exit port on the distal portion of the extended body, and a needle disposed within a lumen in the catheter and configured to be pushed out of the exit port and extend away from a side of the extended body, in which the needle includes a pressure sensor.

20 Claims, 18 Drawing Sheets

(51) Int. Cl.

| | | |
|---|---|---|
| *A61B 8/12* | (2006.01) | |
| *A61B 8/00* | (2006.01) | |
| *A61B 17/06* | (2006.01) | |
| *A61B 17/11* | (2006.01) | |
| *A61B 17/00* | (2006.01) | |
| *A61F 2/07* | (2013.01) | |
| *A61B 90/00* | (2016.01) | |
| *A61B 17/22* | (2006.01) | |

(52) U.S. Cl.
CPC ........ *A61B 8/445* (2013.01); *A61B 17/06066* (2013.01); *A61B 17/11* (2013.01); *A61B 17/3478* (2013.01); *A61B 2017/00022* (2013.01); *A61B 2017/1107* (2013.01); *A61B 2017/1139* (2013.01); *A61B 2017/22054* (2013.01); *A61B 2017/22069* (2013.01); *A61B 2017/22071* (2013.01); *A61B 2090/064* (2016.02); *A61B 2090/3784* (2016.02); *A61B 2562/0247* (2013.01); *A61F 2/07* (2013.01)

(58) Field of Classification Search
CPC ..... A61B 8/445; A61B 8/06; A61B 12/06066; A61B 17/11; A61B 17/3478; A61B 2017/00022; A61B 2017/1107; A61B 2017/1139; A61B 2017/22069; A61B 2017/22071; A61B 2090/064; A61B 2090/3784; A61B 2562/0247; A61F 2/07
See application file for complete search history.

(56) References Cited

U.S. PATENT DOCUMENTS

| | | | |
|---|---|---|---|
| 4,841,977 A | | 6/1989 | Griffith et al. |
| 4,917,097 A | | 4/1990 | Proudian et al. |
| 4,951,677 A | | 8/1990 | Crowley et al. |
| 5,000,185 A | | 3/1991 | Yock |
| 5,125,137 A | | 6/1992 | Corl et al. |
| 5,135,486 A | | 8/1992 | Eberle et al. |
| 5,163,445 A | | 11/1992 | Christian et al. |
| 5,167,233 A | | 12/1992 | Eberle et al. |
| 5,174,295 A | | 12/1992 | Christian et al. |
| 5,176,141 A | | 1/1993 | Bom et al. |
| 5,178,159 A | | 1/1993 | Christian |
| 5,183,048 A | | 2/1993 | Eberle |
| 5,226,421 A | | 7/1993 | Frisbie et al. |
| 5,240,003 A | | 8/1993 | Lancee et al. |
| 5,240,437 A | | 8/1993 | Christian |
| 5,243,988 A | | 9/1993 | Sieben et al. |
| 5,313,949 A | | 5/1994 | Yock |
| 5,353,798 A | | 10/1994 | Sieben |
| 5,368,037 A | | 11/1994 | Eberle et al. |
| 5,373,845 A | | 12/1994 | Gardineer et al. |
| 5,373,849 A | | 12/1994 | Maroney et al. |
| 5,375,602 A | | 12/1994 | Lancee et al. |
| 5,385,148 A | | 1/1995 | Lesh et al. |
| 5,453,575 A | | 9/1995 | O'Donnell et al. |
| 5,846,205 A | | 12/1998 | Curley et al. |
| 5,873,835 A | | 2/1999 | Hastings et al. |
| 5,921,931 A | | 7/1999 | O'Donnell et al. |
| 6,049,958 A | | 4/2000 | Eberle et al. |
| 6,106,476 A | | 8/2000 | Corl et al. |
| 6,200,268 B1 | | 3/2001 | Vince et al. |
| 6,210,339 B1 | | 4/2001 | Kiepen et al. |
| 6,302,875 B1 * | | 10/2001 | Makower ................ A61B 8/12 |
| | | | 604/528 |
| 6,551,250 B2 | | 4/2003 | Khalil |
| 6,726,677 B1 * | | 4/2004 | Flaherty ............... A61B 1/3137 |
| | | | 600/439 |
| 7,074,188 B2 | | 7/2006 | Nair et al. |
| 7,226,417 B1 | | 6/2007 | Eberle et al. |
| 7,711,413 B2 | | 5/2010 | Feldman et al. |
| 7,729,738 B2 | | 6/2010 | Flaherty et al. |
| 7,787,127 B2 | | 8/2010 | Galle |
| 7,846,101 B2 | | 12/2010 | Eberle et al. |
| 7,853,316 B2 | | 12/2010 | Milner et al. |
| 7,914,458 B2 | | 3/2011 | Hossack et al. |
| 7,929,148 B2 | | 4/2011 | Kemp |
| 7,995,210 B2 | | 8/2011 | Tearney et al. |
| 7,999,938 B2 | | 8/2011 | Wang |
| 8,049,900 B2 | | 11/2011 | Kemp et al. |
| 8,108,030 B2 | | 1/2012 | Castella et al. |
| 8,187,191 B2 | | 5/2012 | Hancock et al. |
| 8,346,344 B2 | | 1/2013 | Pfister et al. |
| 8,480,593 B2 | | 7/2013 | Magnin et al. |
| 8,632,468 B2 | | 1/2014 | Glossop et al. |
| 2007/0249939 A1 * | | 10/2007 | Gerbi ................... A61B 8/0841 |
| | | | 600/462 |
| 2007/0260196 A1 * | | 11/2007 | Belsley ............... A61B 17/3478 |
| | | | 604/264 |
| 2008/0180683 A1 | | 7/2008 | Kemp |
| 2008/0291463 A1 | | 11/2008 | Milner et al. |
| 2009/0043191 A1 | | 2/2009 | Castella et al. |
| 2009/0046295 A1 | | 2/2009 | Kemp et al. |
| 2009/0088685 A1 * | | 4/2009 | Kugler ................. A61B 17/221 |
| | | | 604/101.01 |
| 2010/0217117 A1 * | | 8/2010 | Glossop ............... A61B 8/4245 |
| | | | 600/424 |
| 2010/0220334 A1 | | 9/2010 | Condit et al. |
| 2011/0152771 A1 | | 6/2011 | Milner et al. |
| 2012/0013914 A1 | | 1/2012 | Kemp et al. |
| 2012/0136259 A1 | | 5/2012 | Milner et al. |
| 2012/0224751 A1 | | 9/2012 | Kemp et al. |
| 2013/0030303 A1 | | 1/2013 | Ahmed et al. |
| 2013/0060139 A1 | | 3/2013 | Richter |
| 2013/0245533 A1 * | | 9/2013 | Kahn ................... A61M 27/002 |
| | | | 604/8 |
| 2013/0303897 A1 * | | 11/2013 | Pursley ................ A61B 1/3137 |
| | | | 600/425 |
| 2013/0303907 A1 | | 11/2013 | Corl |
| 2015/0141836 A1 * | | 5/2015 | Naumann ............ A61B 8/0841 |
| | | | 600/463 |

FOREIGN PATENT DOCUMENTS

| | | | |
|---|---|---|---|
| WO | WO 99/48545 A1 * | 9/1999 | ............. A61B 17/11 |
| WO | 2006027599 A1 | 3/2006 | |
| WO | 2009076363 A1 | 6/2009 | |

OTHER PUBLICATIONS

Hernández-Guerra, Manuel, et al. (2004). PTFE-covered stents improve TIPS patency in Budd-Chiari syndrome Hepatology, 40(5), 1197-202.

Perz, Joseph F., et al. (2006) The contributions of hepatitis B virus and hepatitis C virus infections to cirrhosis and primary liver cancer worldwide Journal of Hepatology, 45(4), 529-538. doi:10.1016/j.jhep.2006.05.013.

Yin, L. et al., "The Surgical Treatment for Portal Hypertension: A Systematic Review and Meta-Analysis", 2013, China.

Jalan, R. et al., "TIPSS 10 years on", 2018, pp. 578-581.

* cited by examiner 105 trachea
109 lung
113 heart
117 liver
121 stomach
125 small intestines
127 large intestines 117 liver
121 stomach
131 duodenum
139 jejunum
145 portal vein
149 hepatic artery
161 pancreas
165 spleen

DEVICES AND METHODS FOR INTRAHEPATIC SHUNTS

CROSS-REFERENCE TO RELATED APPLICATIONS

This application claims priority to, and the benefit of, U.S. Provisional Application No. 62/024,520, filed Jul. 15, 2014, which is incorporated by reference in its entirety.

FIELD OF THE INVENTION

The invention relates to devices and methods for creating intrahepatic shunts.

BACKGROUND

A person with cirrhosis of the liver may have bloody vomit or stool. Untreated, cirrhosis can cause shock and death. Liver cirrhosis—which can result from alcoholism, hepatitis, disease, or unknown causes—is characterized by scar tissue and nodules in the liver that lead to loss of liver function. Liver cirrhosis presents resistance to blood flow through the portal venous system, causing undue pressure, or portal hypertension. Effects of portal hypertension include collateral blood flow that swells the vessels around the esophagus. Swollen esophageal vessels, or varices, are known to burst, resulting in variceal bleeding. After esophageal varices have bled once, there is a high risk of bleeding again. Bleeding varices can appear as bloody stool and vomit and variceal bleeding can lead to shock and death. Thus, liver cirrhosis, portal hypertension, and esophageal varices are associated with patient mortality. In fact, twenty percent of cirrhotics with acute variceal hemorrhage die within six weeks. See Loffroy, 2013, Transjugular intrahepatic portosystemic shunt for the management of acute variceal hemorrhage, World J Gastroent 19(37):6131-6143. One candidate treatment procedure for variceal hemorrhage is the transjugular intrahepatic portosystemic shunt (TIPS) procedure discussed in Loffroy. However, Loffroy reports that the TIPS procedure can be associated with troubling outcomes such as stent displacement, 10 to 29% relapse rates, or cardiac failure.

SUMMARY

The invention provides methods and devices for creating a shunt (that is, a new passage) from a portal vein of a patient to a hepatic vein using a device with intravascular imaging capabilities and blood pressure measurement capabilities. The integration of intravascular imaging in a catheter with a needle for creating the shunt aids in the precise placement of the shunt between the portal vein and the hepatic vein. The integration of a pressure sensor helps determine the successful creation of a shunt for the relief of portal hypertension. The newly-formed shunt allows blood flow to bypass the liver, and the shunt may be expanded or preserved using a balloon, stent, or both. The use of an intravascular imaging device on the catheter that carries the needle to the shunt site gives a practitioner three-dimensional information about a spatial relationship between the portal vein and the hepatic vein—where prior art procedures had only two-dimensional angiography information—allowing the practitioner to use the needle to precisely and accurately pierce through the tissue and create the shunt. Additionally, the catheter or a lumen through needle which extends from the catheter may be used to place a guidewire into the shunt, allowing a balloon and/or stent to be delivered to the shunt. Since the shunt was created using the 3D guidance provided by intravascular imaging on the shunt-creation device, the shunt and any balloon or stent is located correctly in a time-effective manner. Since the shunt is timely placed in the correct location, it may successfully relieve portal hypertension and avoid variceal hemorrhage. Thus treatment using devices and methods of the invention may relieve symptoms and decrease the mortality rates of cirrhosis, portal hypertension, or variceal hemorrhage.

In certain aspects, the invention provides a method of creating an intrahepatic portosystemic shunt. The method includes directing a catheter down a jugular vein and into a hepatic vein of a patient, operating an imaging device such as an ultrasound transducer disposed on the catheter from within the hepatic vein to obtain an image of a portal vein of the patient, and extending a needle member out from within the catheter to create a shunt defining a passageway through which blood can flow from the portal vein to the hepatic vein. A pressure sensor on the needle member may be used to verify a change in pressure that indicates successful creation of the shunt. Preferably, the needle member extends away from a side of the catheter by a distance of at least one centimeter. The needle member may be configured to exit from a port on the catheter and the imaging device may be operable to capture the image of the portal vein prior to and during the needle member being extended from the catheter. The method may include inserting a guidewire through a lumen within the needle member, removing the needle member from the shunt while leaving the guidewire within the shunt, and using the guidewire to insert a balloon catheter comprising a balloon into the shunt. The balloon may be used to expand a cross-sectional area of the shunt, after which the balloon catheter is removed from the shunt and a stent is delivered to the shunt.

In some embodiments, the catheter comprises a needle exit port in proximity to the imaging device and the needle—when extended from the catheter through the needle exit port—assumes a curved shape and extends a distance away from the needle exit port. The needle extends from the needle exit port in a direction away from the catheter (e.g., by a distance of at least about 1 cm). A distal tip of the needle, when the needle is extended from the catheter, may define an angle θ with the catheter where θ is at least 65° and is preferably at least 75°. In certain embodiments, the needle comprises a shape memory metal.

Aspects of the invention provide an apparatus for creating an intrahepatic portosystemic shunt. The apparatus includes a catheter with an extended body configured for insertion down a jugular vein into a hepatic vein of a patient, an intravascular imaging device (e.g., an IVUS transducer) on a distal portion of the extended body, a needle exit port on the distal portion of the extended body, and a needle disposed within a lumen in the catheter and configured to be pushed out of the exit port and extend away from a side of the extended body by a distance of at least one centimeter. The apparatus includes a pressure sensor on the needle. The needle may include a shape memory metal (e.g., nitinol) that assumes a curved shape as the needle exits the exit port. In certain embodiments, the needle has a lumen that is dimensioned to receive a guidewire extending therethrough.

Preferably, the needle is dimensioned to extend from the exit port away from the side of the catheter body through tissue and into a portal vein. The needle may include a sharp or beveled tip configured to pierce through the tissue between the hepatic vein and the portal vein thereby creating a portosystemic shunt. The needle may include a lumen for delivering a treatment agent (e.g., a thrombolytic agent) to the tissue.

The imaging device (e.g., IVUS transducer) may be operable to produce an image of the portal vein when within the hepatic vein. A proximal end of the catheter may be connected to an imaging system comprising a processor and a display, which can display images produced by the IVUS transducer.

The pressure sensor may further include a functional measurement instrument for measuring fluid velocity. An apparatus of the invention may be provided with a positioning mechanism, such as a multi-balloon positioning mechanism that can brace and orient the needle.

The invention provides methods and devices for creating a shunt from a portal vein of a patient to a hepatic vein using a device with intravascular imaging capabilities and a multi-balloon positioning mechanism. The integration of intravascular imaging in a catheter with a needle for creating the shunt aids in the precise placement of the shunt between the portal vein and the hepatic vein. The integration of a multi-balloon positioning mechanism allows for adjustment of position of the shunt-creation needle by modulating the relative inflation of two (or more) balloons extending along the body of the device. The use of an intravascular imaging device on the catheter that carries the needle to the shunt site gives a practitioner three-dimensional information about a spatial relationship between the portal vein and the hepatic vein. The multi-balloon positioning device aids in bracing the catheter within the hepatic vein, giving the device purchase, thus aiding the needle in precisely and accurately piercing through the tissue to create the shunt.

In some aspects, the invention provides a device for creating an intrahepatic portosystemic shunt. The device includes a multi-balloon positioning mechanism. The device has a catheter with an extended body configured for insertion down a jugular vein into a hepatic vein of a patient. A distal portion of the extended body includes an intravascular imaging device, a needle exit port, and a needle disposed within a lumen in the catheter. The needle is configured to be pushed out of the exit port and extend away from a side of the extended body. The device includes a first balloon and a second balloon disposed in parallel to one another along a length of the extended body opposed to the needle exit port, wherein inflation of the first balloon and the second balloon biases a portion of the extended body towards a side of the hepatic vein. Preferably, the needle extends away from the side of the extended body by a distance of at least 1 cm. The needle may include a shape memory material that assumes a curved shape as the needle exits the exit port. In certain embodiments, the device includes a pressure sensor disposed on the needle. The intravascular imaging device may use an ultrasound transducer to produce an image of a portal vein when within the hepatic vein.

Aspects of the invention provide a method of creating an intrahepatic portosystemic shunt by directing a catheter down a jugular vein and into a hepatic vein of a patient and operating an imaging device disposed on the catheter from within the hepatic vein to obtain an image of a portal vein of the patient. The method includes inflating at least a first balloon and a second balloon to position the catheter within the hepatic vein, where the first balloon and the second balloon disposed on the catheter substantially opposed to a needle exit port. A needle is extended out from the needle exit port to create a shunt defining a passageway through which blood can flow from the portal vein to the hepatic vein. Preferably, the first balloon and the second balloon extend along the body of the catheter substantially parallel to one another and spaced apart from one another and each spaced apart from the needle exit port along a circumference around the catheter. The method may include adjusting the orientation of the needle by adjusting the relative inflation of the first balloon and the second balloon.

DETAILED DESCRIPTION

Figure 1:
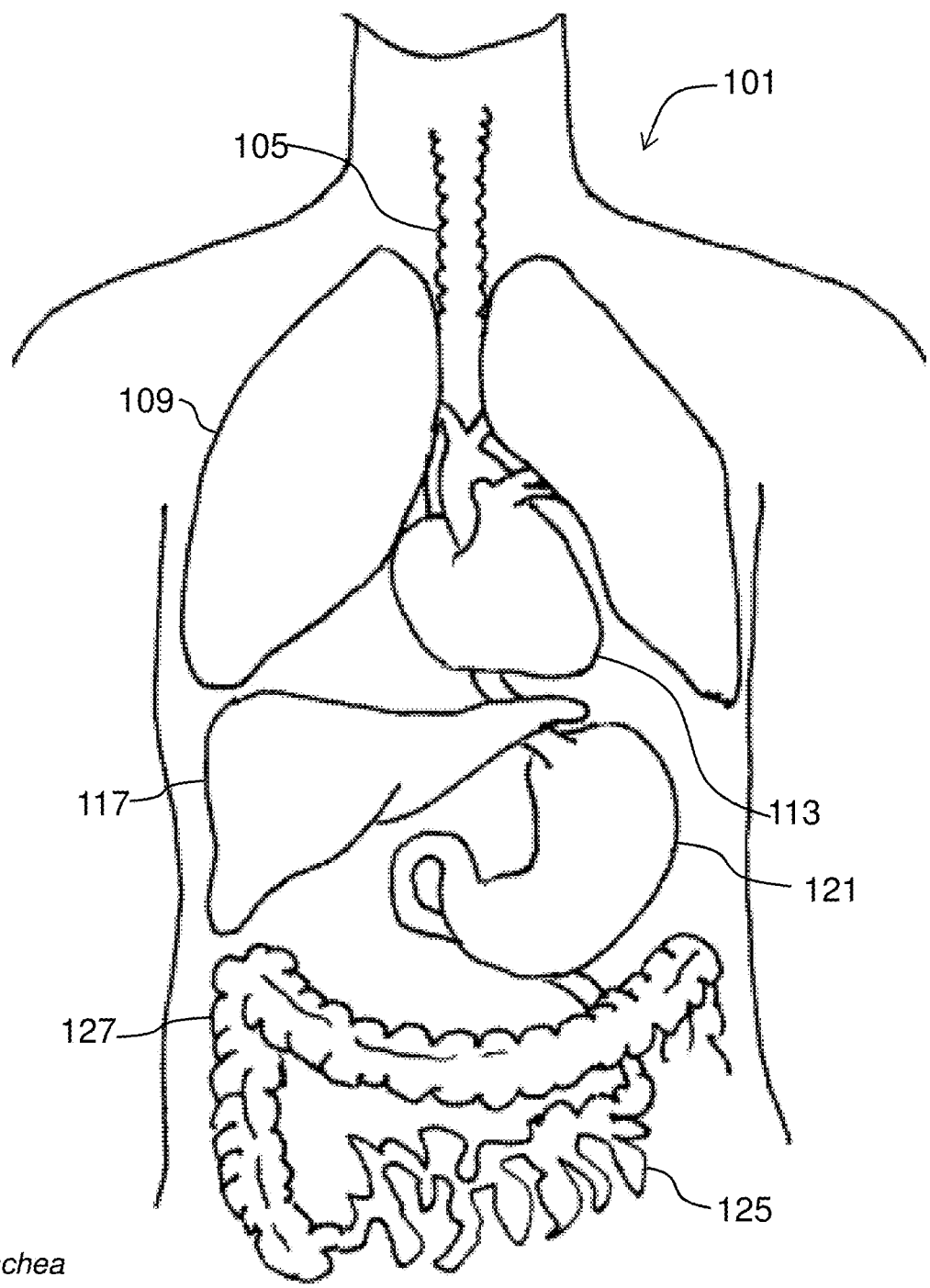
FIG. 1 shows organs of the human body.
Figure 2:
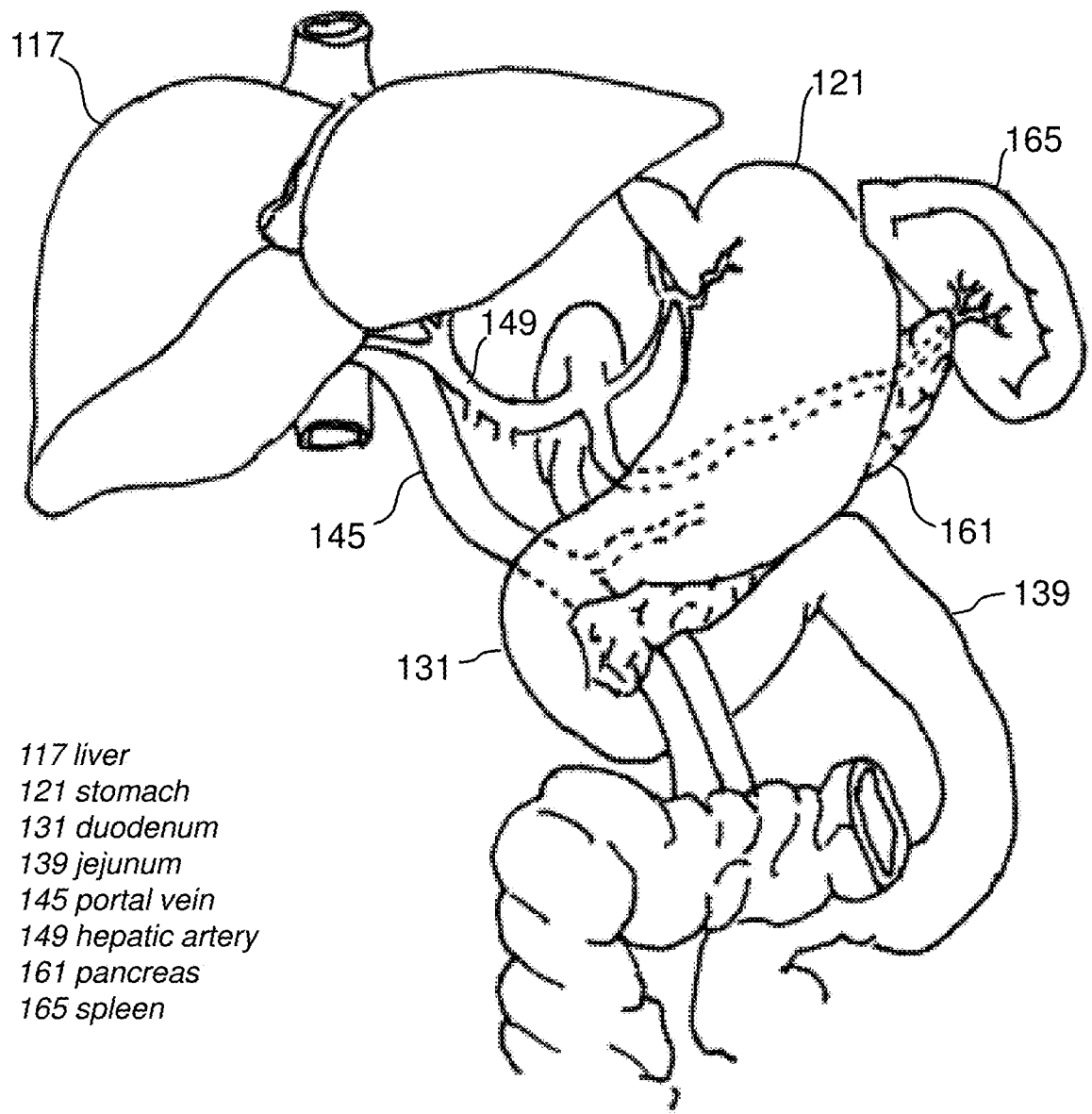
FIG. 2 depicts elements of the portal venous system.
Figure 3:
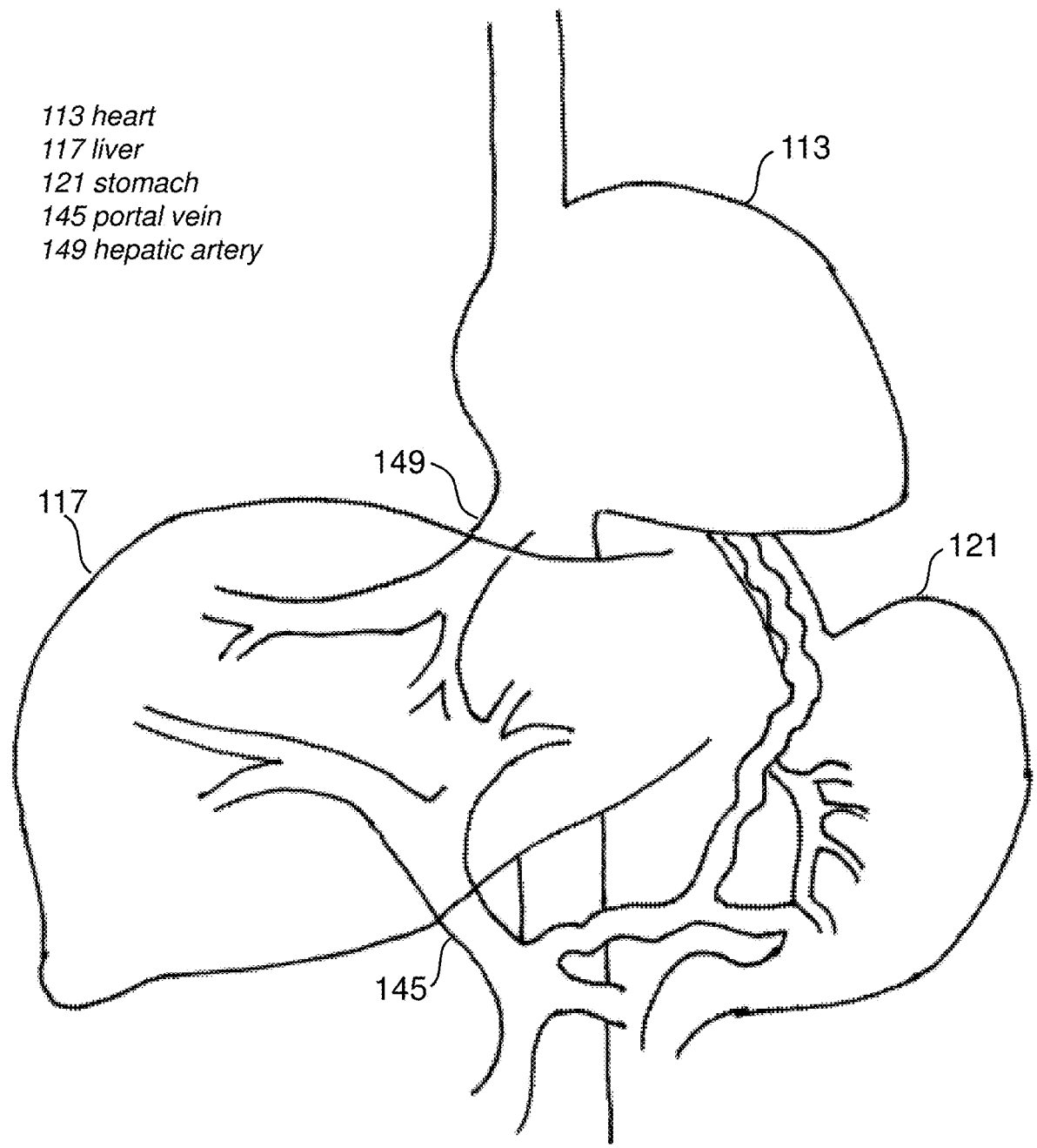
FIG. 3 illustrates the liver and a typical hepatic artery as well as portal vein.

The invention provides a crossing catheter with intravascular imaging for use in a transjugular intrahepatic portosystemic shunt (TIPS) procedure and methods for performing a TIPS procedure using such a catheter. Methods and devices of the invention may be used to treat a patient with cirrhosis, portal hypertension, bleeding of esophageal varices and other related conditions. A device of the invention provides a crossing catheter with a wire extension, in which the wire can be used to pierce out of the first vessel and into the second to create new connections between two blood vessels in the liver. FIGS. 1-3 are included to illustrate a typical arrangement of a patient's organs and relevant portions of the portal venous system.

FIG. 1 shows important organs of the human body 101. A patient's trachea 105 extends down to lungs 109, located above liver 117. Heart 113 is between the lungs while the large intestine 127 and small intestines 125 may be found a lower portion of the torso. The invention includes the insight that three-dimensional imaging of organ systems depicted here provide improvements to methods and systems for treating those systems, as proper treatment is better served by using a three-dimensional representation of these components that the simplified 2D information provided by angiography.

FIG. 2 introduces elements of the portal venous system in more detail, showing hepatic artery 149, which carries blood from the liver back to the vena cava and the heart 113. Portal vein 145 carries blood from the intestines and intra-abdominal organs to the liver 117. For ease of visualization, the figure includes stomach 121, pancreas 161, and the spleen 165. Duodenum 131 connects stomach 121 to the jejunum 139 of small intestines 125.

FIG. 3 zooms in on liver 117 and specifically shows a typical hepatic artery 149 extending to heart 113 as well as portal vein 145, extending from the spleen 165 and the gastrointestinal tract. Portal vein 145 is a blood vessel that conducts nutrient-rich blood from the gastrointestinal tract and spleen to the liver. Liver 117 processes nutrients in the blood and filters toxins. The liver receives about 75% of its blood through the hepatic portal vein, with the remainder coming from the hepatic artery proper. The blood leaves the liver to the heart in the hepatic veins. It is noted that portal vein 145 is not a true vein, as it conducts blood to capillary beds in the liver and not directly to the heart. Portal vein 145 is usually formed by the confluence of the superior mesenteric and splenic veins and also receives blood from the inferior mesenteric, gastric, and cystic veins. The invention includes the insight that the relationship between hepatic artery 149 and portal vein 145 is more complex than can be simply represented in two dimensions. All or any portion of one may be disposed posterior or anterior to all or any portion of the other. The invention provides systems and methods that use 3D intravascular imaging in a TIPS procedure.

Figure 4:
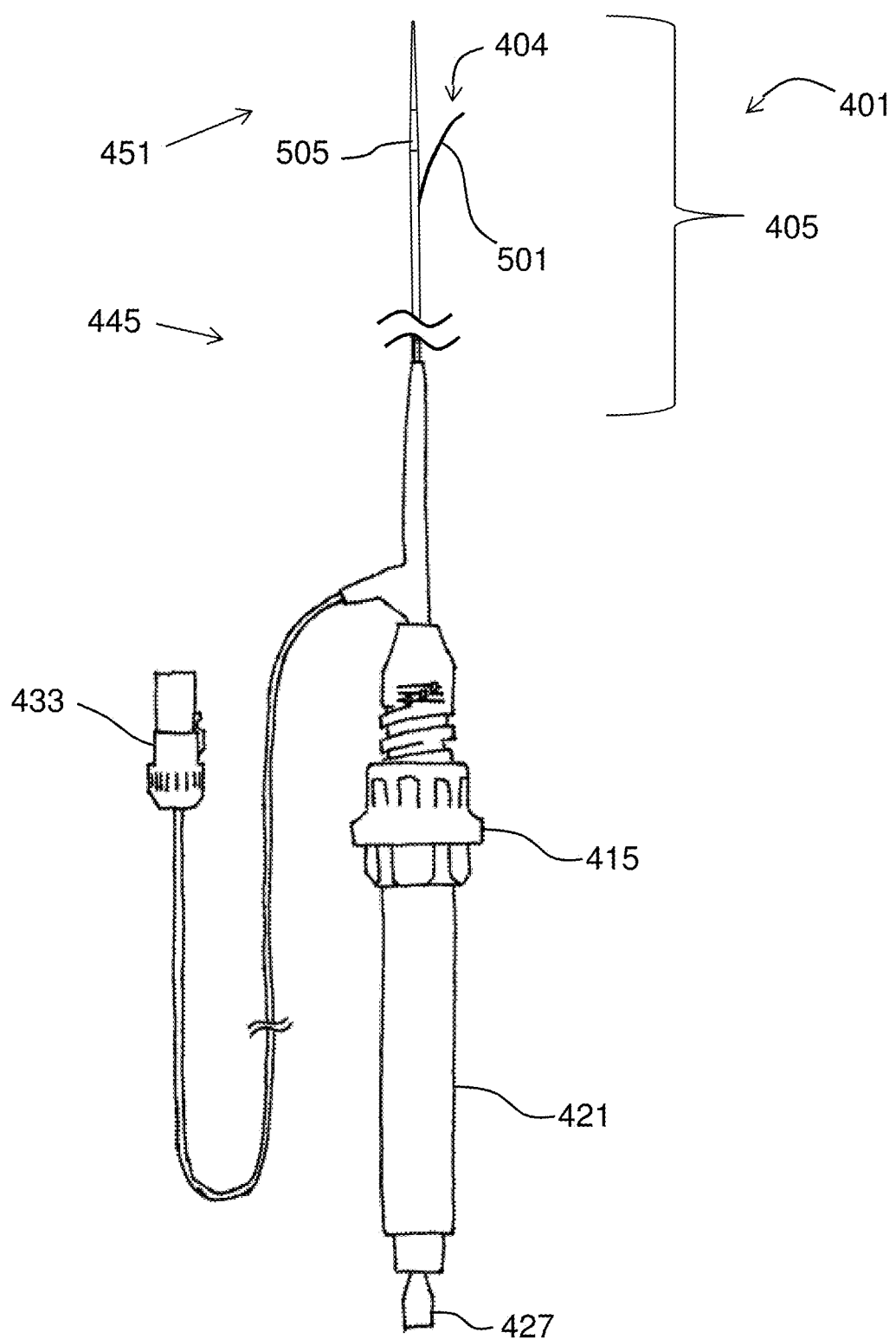
FIG. 4 depicts an apparatus for creating an intrahepatic portosystemic shunt.

FIG. 4 depicts an apparatus 401 for creating an intrahepatic portosystemic shunt. Apparatus 401 may be used to create the access between the two vessels. Apparatus 401 includes a catheter with an extended body 405 having a distal portion 451 and a proximal portion 445. Distal portion 451 includes an exit port from which a needle 501 may extend as well as an imaging device 505. Distal portion 451 also includes a pressure sensor 404, which may be mounted on the needle 501 (or elsewhere on the apparatus 401). The catheter extends from handle 421 and may include a needle deployment portion 415 having needle depth markers and a locking needle stop ring. At the base of handle 421 is an access port 427 opening to a needle guide wire lumen. Connected to and extending from proximal portion 445 is a connector 433 for connection to an imaging instrument.

Figure 5:
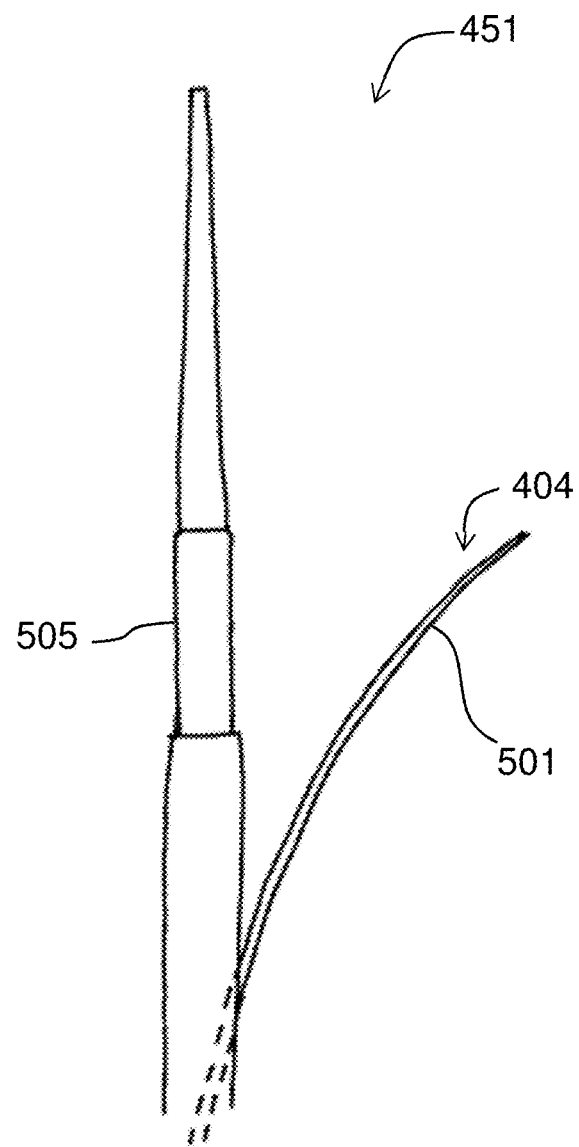
FIG. 5 gives a detailed view of a needle 501 extended from a catheter.

FIG. 5 gives a detailed view of distal portion 451, showing needle 501 extended from the distal portion 451 of the extended catheter body 405 with in intravascular imaging device 505 on extended catheter body 405. In the depicted embodiment, intravascular imaging device 505 is disposed just distal to a needle exit port. The needle 501 may have the pressure sensor 404 disposed on a distal portion of the needle. The pressure sensor 404 can be formed of a crystal semiconductor material having a recess therein and forming a diaphragm bordered by a rim. A reinforcing member is bonded to the crystal and reinforces the rim of the crystal and has a cavity therein underlying the diaphragm and exposed to the diaphragm. A resistor having opposite ends is carried by the crystal and has a portion thereof overlying a portion of the diaphragm. Electrical conductor wires can be connected to opposite ends of the resistor and extend within the needle 501 to the proximal portion of the apparatus 401. Additional details of suitable pressure sensors that may be used with devices of the invention are described in U.S. Pat. No. 6,106,476. Further discussion of the pressure sensor is given below with respect to FIG. 12. Device 401 further includes an imaging device 505 to perform intravascular imaging.

Any suitable imaging modality may be provided by intravascular imaging device 505 such as, for example, optical coherence tomography, optic-acoustical imaging, ultrasound, or any others. In a preferred embodiment, imaging device 505 operates via intravascular ultrasound (IVSU).

The imaging device 505 may use phased-array IVUS device or rotational IVUS. IVUS imaging provides a tool for assessing tissue of the human body from within to determine the need for treatment, to guide an intervention, or to assess its effectiveness. Where intravascular imaging device 505 uses IVUS, catheter 401 including one or more IVUS transducer is introduced into the vessel and guided to the area to be imaged. The transducers emit and then receive backscattered ultrasonic energy in order to create an image of the vessel of interest. Ultrasonic waves are partially reflected by discontinuities arising from tissue structures (such as the various layers of the vessel wall) and other features of interest. Echoes from the reflected waves are received by the transducer and passed along to an IVUS imaging system. The imaging system processes the received ultrasound echoes to produce a 360-degree, three-dimensional image of the vessel where the device is placed. IVUS imaging devices suitable for modification for use with the invention are described in U.S. Pat. Nos. 4,794,931; 5,000,185; 5,313,949; 5,243,988; 5,353,798; 4,951,677; 4,841,977; 5,373,849; 5,176,141; 5,240,003; 5,375,602; 5,373,845; 5,453,575; 5,368,037; 5,183,048; 5,167,233; 4,917,097; and 5,135,486, each incorporated by reference.

There are two general types of IVUS devices in use today: rotational and solid-state (also known as synthetic aperture phased array). For a typical rotational IVUS device, a single ultrasound transducer element is located at the tip of a flexible driveshaft that spins inside a plastic sheath inserted into the vessel of interest. The transducer element is oriented such that the ultrasound beam propagates generally perpendicular to the axis of catheter 401. A fluid-filled sheath may protect the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

In contrast, solid-state IVUS devices carry a transducer complex that includes an array of ultrasound transducers distributed around the circumference of the device connected to a set of transducer controllers. The transducer controllers select transducer sets for transmitting an ultrasound pulse and for receiving the echo signal. By stepping through a sequence of transmit and receive sets, the solid-state IVUS system can synthesize the effect of a mechanically scanned transducer element but without moving parts. The same transducer elements can be used to acquire different types of intravascular data. The different types of intravascular data are acquired based on different manners of operation of the transducer elements. The solid-state scanner can be wired directly to the imaging system with a simple electrical cable and a standard detachable electrical connector.

The transducer subassembly can include either a single transducer or an array. The transducer elements can be used to acquire different types of intravascular data, such as flow data, motion data and structural image data. For example, the different types of intravascular data are acquired based on different manners of operation of the transducer elements. For example, in a gray-scale imaging mode, the transducer elements transmit in a certain sequence one gray-scale IVUS image. Methods for constructing IVUS images are well-known in the art, and are described, for example in U.S. Pat. Nos. 8,187,191; 7,074,188; 6,200,268, each incorporated by reference. The imaging system allows one image (or frame) of flow data to be acquired. Methods and processes for acquiring different types of intravascular data, including operation of the transducer elements in the different modes (e.g., gray-scale imaging mode, flow imaging mode, etc.) consistent with the present invention are further described in U.S. Pat. No. 7,914,458 to Hossack; U.S. Pat. No. 7,846,101 to Eberle; U.S. Pat. No. 7,226,417 to Eberle; U.S. Pat. No. 6,049,958 to Eberle; and U.S. Pat. No. 5,846,205 to Curley, each incorporated by reference.

The acquisition of each flow frame of data is interlaced with an IVUS gray scale frame of data. Operating an IVUS catheter to acquire flow data and constructing images of that data is further described in U.S. Pat. No. 5,921,931 to O'Donnell and U.S. Pub. 2013/0303907 to Corl, each incorporated by reference. Commercially available software for operating an IVUS catheter in flow mode and displaying flow data is CHROMAFLOW (IVUS fluid flow display software offered by the Volcano Corporation).

In certain embodiments, the imaging device is an OCT device. OCT systems and methods are generally described in U.S. Pat. Nos. 8,108,030; 8,049,900; 7,929,148; 7,853,316; 7,711,413; U.S. Pub. 2011/0152771; U.S. Pub. 2010/0220334; U.S. Pub. 2009/0043191; U.S. Pub. 2008/0291463; U.S. Pub. 2008/0180683; U.S. Pub. 2012/0224751; U.S. Pub. 2012/0136259; U.S. Pub. 2012/0013914; U.S. Pub. 2011/0152771; and U.S. Pub. 2009/0046295, each incorporated by reference.

OCT systems of the invention include a light source. The light source may be any light source generally used with OCT. Exemplary light sources include a narrow line width tunable laser source or a superluminescent diode source. Examples of narrow line width tunable laser sources include, but are not limited to, lasers having a Bragg diffraction grating or a deformable membrane, lasers having a spectral dispersion component (e.g., a prism), or Fabry—Perot based tuning laser.

OCT systems of the invention also include an interferometer. The interferometer may be any interferometer generally used with OCT. Typically, the interferometer will have a differential beam path for the light or a common beam path for the light. In either case, the interferometer is operably coupled to the light source. In a differential beam path layout, light from a broad band light source or tunable laser source is input into an interferometer with a portion of light directed to a sample and the other portion directed to a reference surface. A distal end of an optical fiber is interfaced with a catheter for interrogation of the target tissue during a catheterization procedure. The reflected light from the tissue is recombined with the signal from the reference surface forming interference fringes (measured by a photovoltaic detector) allowing precise depth-resolved imaging of the target tissue on a micron scale. Exemplary differential beam path interferometers are Mach—Zehnder interferometers and Michelson interferometers.

The differential beam path optical layout of the interferometer includes a sample arm and a reference arm. The sample arm is extends through catheter 401. In the interferometer, there is a circulator where the emitted light is split to the sample arm and the reference arm. The system also includes a circulator that directs light to the sample and receives reflected light from the sample and directs it toward a detector. The system also includes a circulator that directs light to the reference surface and received reflected light from the reference surface and directs it toward the detector. There is also a circulator at the point at which reflected light from the sample and reflected light from the reference are recombined and directed to the detector.

In a common beam path system, rather than splitting a portion of the light to a reference arm, all of the produced light travels through a single optical fiber. Within the single fiber is a reflecting surface. A portion of the light is reflected off that surface prior to reaching a target tissue (reference) and a remaining portion of the light passes through the reflecting surface and reaches the target tissue. The reflected light from the tissue recombines with the signal from the reference forming interference fringes allowing precise depth-resolved imaging of the target tissue on a micron scale. Common beam path interferometers are further described in U.S. Pat. Nos. 7,999,938; 7,995,210; and 7,787,127, each incorporated by reference The common beam path optical layout of the interferometer includes a single array of optical fibers that are connected to a circulator. The array of optical fibers are configured to accommodate and couple to a catheter. The circulator directs light transmitted from the light source through the array of optical fibers of the common beam path optical layout to a sample and reference, and receives the reflected light from the sample and reference and directs it to the detector.

OCT systems of the invention include a detector. The detector includes photodetection electronics that may include for example photodiodes to convert light to electronic impulses and a chip such as a field programmable gate array to convert the electronic impulses into computer-readable 3D image data. OCT systems of the invention may conduct any form of OCT known in the art. One manner for conducting OCT may be Swept-Source OCT ("SS-OCT"). SS-OCT time-encodes the wavenumber (or optical frequency) by rapidly tuning a narrowband light source over a broad optical bandwidth. The high speed tunable laser sources for SS-OCT exhibit a nonlinear or non-uniform wavenumber vs. time [k(t)] characteristic. As such, SS-OCT interferograms sampled uniformly in time [S(t), e.g., using an internal digitizer clock] must be remapped to S(k) before Fourier transforming into the path length (z) domain used to generate the OCT image.

Other imaging modalities that may be provided by intravascular imaging device 505 may include spectroscopic devices, (including fluorescence, absorption, scattering, and Raman spectroscopies), Forward-Looking IVUS (FLIVUS), high intensity focused ultrasound (HIFU), radiofrequency, optical light-based imaging, magnetic resonance, radiography, nuclear imaging, photoacoustic imaging, electrical impedance tomography, or others. As discussed above, by including intravascular 3D imaging on a device for creating an intrahepatic shunt, the ability to create a shunt quickly and correctly may be improved as a practitioner may view a 3D image of the portal vein from the hepatic vein on a monitor while guiding needle 501 from the hepatic vein to the portal vein.

Figure 6:
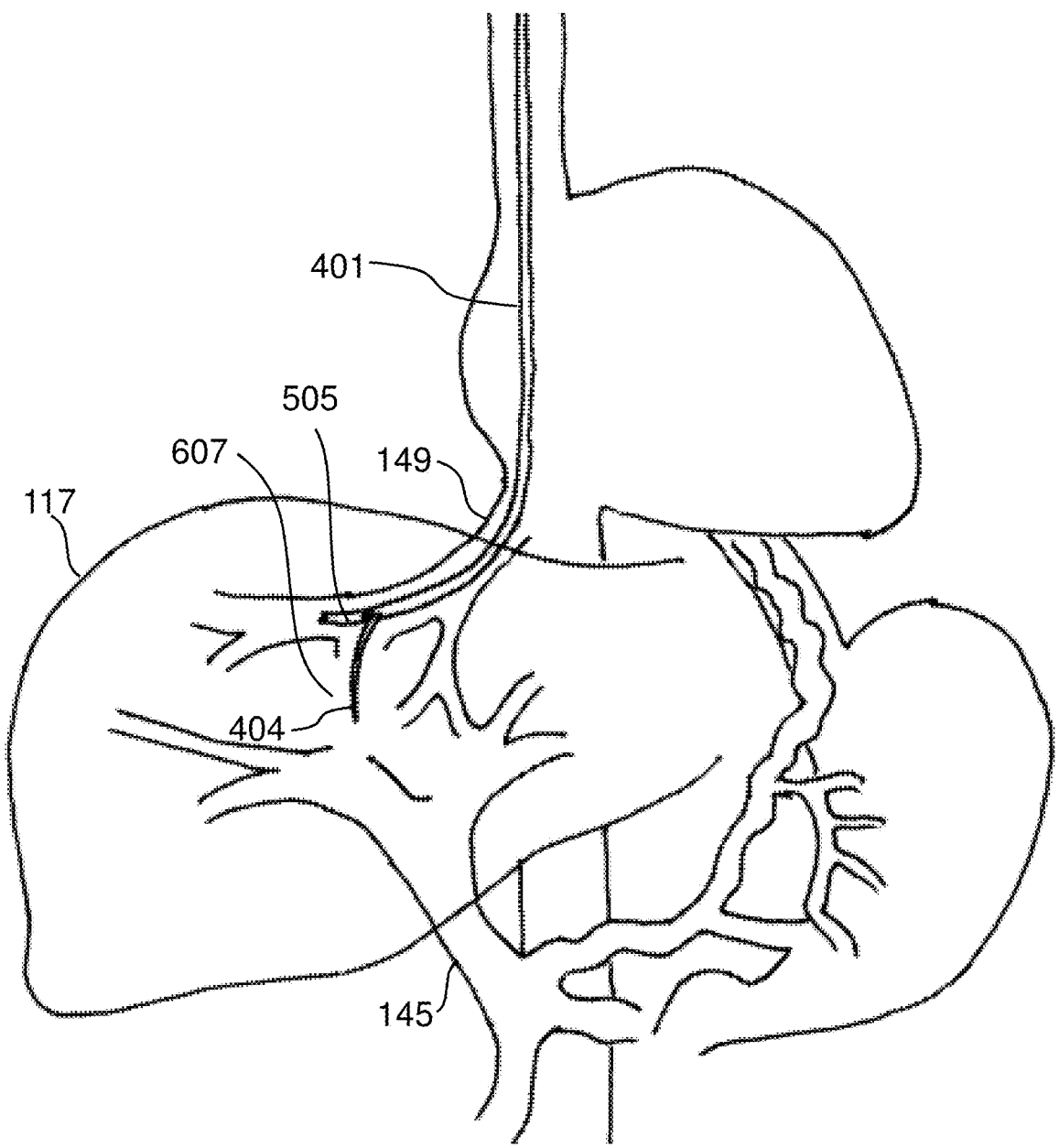
FIG. 6 illustrates use of apparatus for creating an intrahepatic portosystemic shunt.

FIG. 6 illustrates use of apparatus 401 in a method of creating an intrahepatic portosystemic shunt 607. With FIG. 6 for references, after entry into the internal jugular vein, catheter 401 is introduced and guided through the superior vena cava and into a hepatic vein according to methods of the invention.

Figure 7:
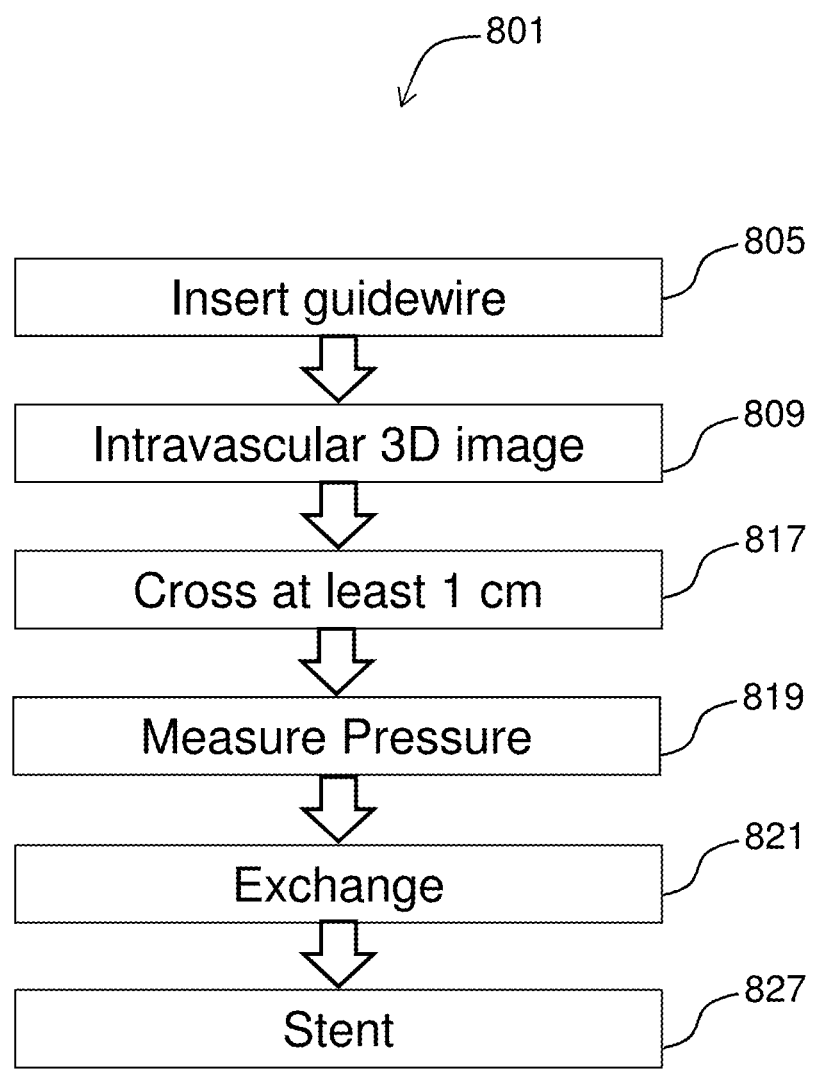
FIG. 7 diagrams a method for creating an intrahepatic portosystemic shunt.

FIG. 7 diagrams steps of a method 801 for creating an intrahepatic portosystemic shunt 607. In method 801, a guidewire may be inserted 805 down the jugular vein of patient 101 from the neck (optionally using X-ray guidance to complement the intravascular imaging). Intravascular imaging device 505 is operated 809 to obtain a 3D image of the tissue, aiding the practitioner in viewing portal vein 145 from hepatic vein 149. Needle 501 is extended from apparatus 401 and used to cross 817 the tissue between portal vein 145 and hepatic vein 149, thus creating shunt 607. Pressure sensor 404 can be used to measure 819 pressure and the measure of pressure may show successful creation of the shunt. Needle 501 is extended from catheter 401 and used to puncture the liver from a central portion of hepatic vein 149 and enter the main portal branch, usually the right portal vein 145. An important advantage in using apparatus 401 lies within its intravascular imaging capabilities. A practitioner can place apparatus 401 in the first vessel, see the second vessel using IVUS (the sound waves can travel through the liver tissue to permit visualization of the second vessel), and then use the needle member 501 to create the inter-vessel access. It is noted that use of intravascular imaging on device 401 aids in avoiding laceration of the liver capsule with needle 501 or entering the hepatic artery. Intravascular imaging is useful in making the TIPS tract intraparenchymal, or dilatation of the extrahepatic portion of the portal vein could result in undesirable exsanguination. Use of the invention may reduce the use of fluoro and reduce the overall procedure time. Once the shunt is created, catheter 401 is exchanged 821 over a guidewire for a catheter to deliver a balloon, stent, or both, and a stent may be placed 827 in the shunt.

Figure 8:
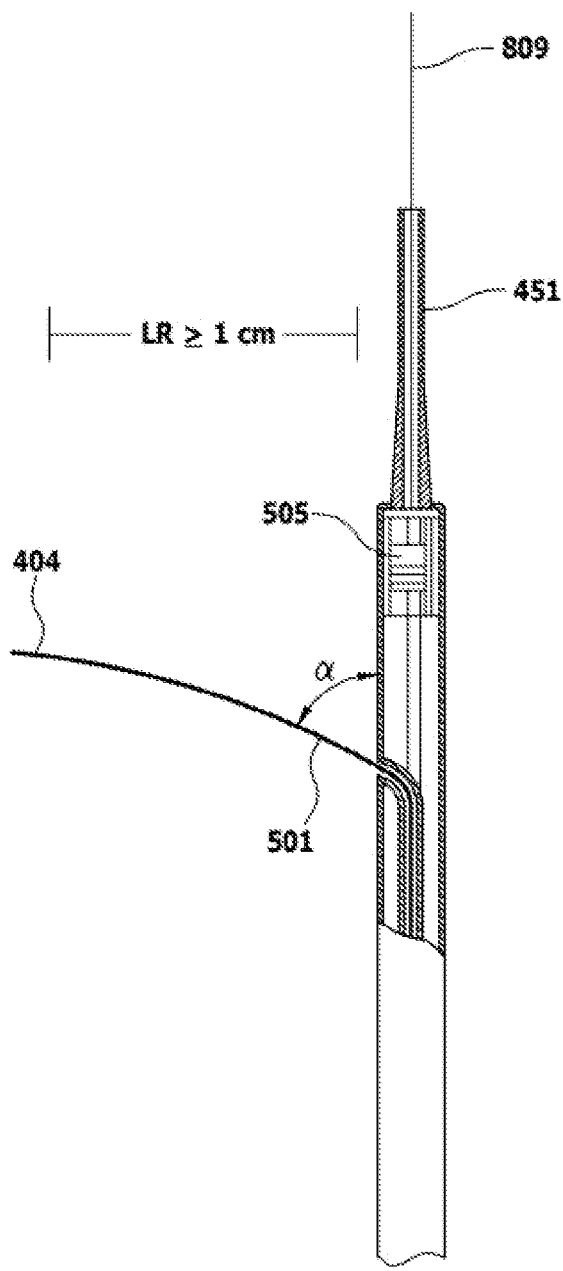
FIG. 8 shows a needle extending from an exit port on a catheter.

FIG. 8 shows needle 501 extending from an exit port on a side of distal portion 451 of catheter 401. Also shown in FIG. 8 is guidewire 801 over which catheter 401 may be advanced, or which may be advanced through catheter 401. It is noted that intravascular imaging sensor 505—which may include an ultrasound transducer—is depicted as being disposed just distal to the exit port, although it can be located in other places. Needle 501 includes pressure sensor 404. FIG. 8 illustrates that a dimension of needle 501 provides a lateral reach (LR) of at least 1 cm. This allows needle 501 to reach portal vein 145. In the portal vein, needle 501 can be advanced to create the shunt. In certain embodiments, device 401 includes a needle 501 that provides a lateral reach of at least about 1.5 cm and it may be 2 cm or greater. To aid in creating the shunt, needle 501 should preferably extend substantially oblique to the body of catheter 401.

Figure 9:
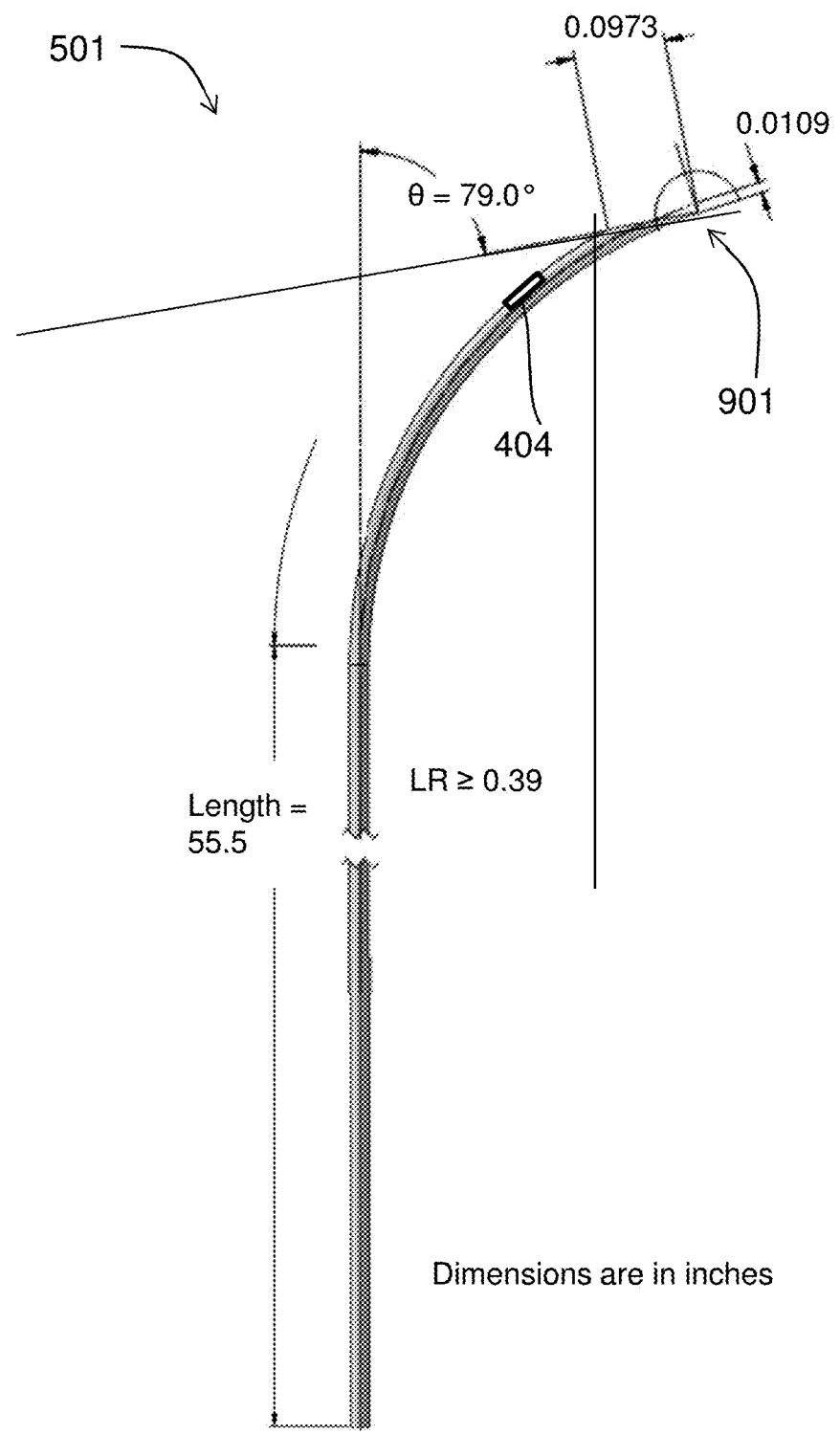
FIG. 9 illustrates a curved shape of a needle.

FIG. 9 illustrates a curved shape of needle 501 that defines an angle of about 79° with an axis of catheter 401 and also defines a lateral reach of at least about 0.39 inches or about 1 cm. Needle 501 preferably includes a shape-memory metal such as nitinol such that needle 501 is maintained with a shape of catheter 401 when needle 501 is retained within catheter 401, but so that needle 501 assumes a curved shape as illustrated in FIG. 9 when extended from catheter 401. To aid in piercing through the liver tissue, needle 501 preferably includes a sharpened or beveled tip 901.

Figure 10:
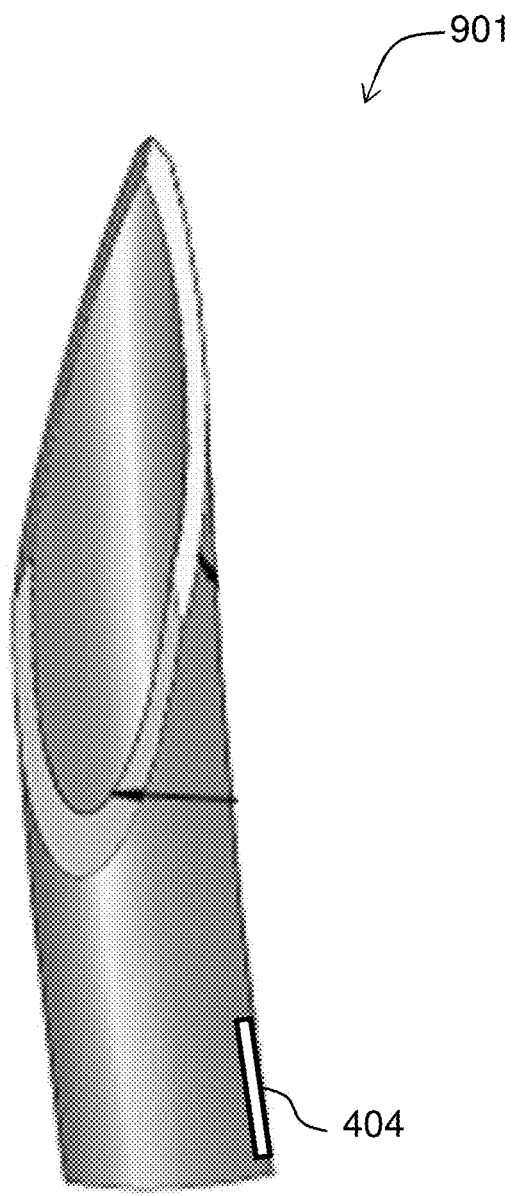
FIG. 10 shows a beveled tip on a needle.

FIG. 10 illustrates beveled tip 901 on needle 501. With reference back to FIG. 9, it will be appreciated that beveled tip 901 when needle 501 is extended can define an angle θ with an axis of catheter 401 and a proximal portion of needle 501. For effective creation of shunt 607, angle θ is preferably greater than about 55° and more preferably at least 75° or more. In the depicted embodiment, angle θ is about 79°. Once needle 501 has created shunt 607, apparatus 401 may be exchanged 821 with a catheter for delivering a balloon, stent, or both. The needle tract may then be dilated by a balloon catheter, establishing a connection between the portal and systemic circulation directly inside the liver parenchyma. The parenchymal tract may be kept open by insertion of a stent. See Hernandez-Guerra, 2004, PTFE-covered stents improve patency in Budd-Chiari syndrome, Hepatology 40:1197-1202.

Figure 11:
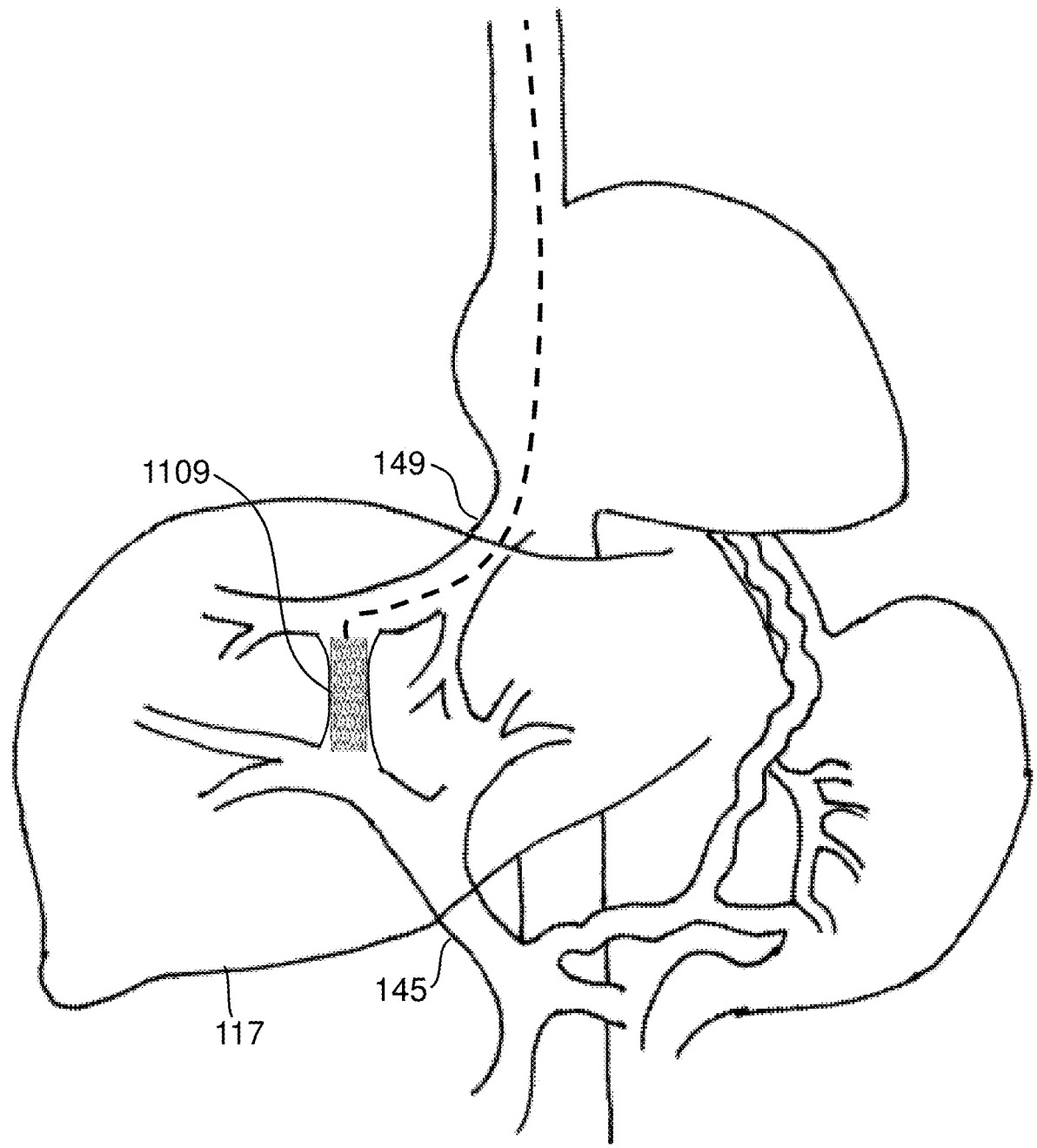
FIG. 11 diagrams a stent in a shunt.

FIG. 11 illustrates stent 1109 in shunt 607. The dotted line represents the path defined by the guidewire and the path followed by imaging/shunt creation catheter 401 as well as a stent delivery catheter or balloon catheter, and those devices are not drawn in FIG. 11 Stent 1109 preferably defines a generally cylindrical shape. A PTFE-covered stent may be used, a bare metal stent, or any other suitable stent. By alternate separation of the intersecting points of the lattice, a flexibility of the axis of shunt stent 1109 is achieved, so that it also can be used in a curved shunt. An uncovered part of stent 1109 about 2 cm long may protrude into the portal vein 145 to anchor stent 1109 and aid blood flow. The shunt diameter may be finalized by balloon dilatation of stent 1109. Stent 1109 diverts portal blood into systemic circulation, resulting in the decompression of portal hypertension. The size of the balloon catheter is usually 8 mm. In certain embodiments, device 401 or a guidewire that has been extended through the catheter includes a functional measurement sensor to measure pressure, velocity, or both.

In some embodiments, a pressure sensor (or a flow velocity sensor, or a combination sensor) is additionally or alternatively placed on a catheter of the device or a guidewire for use in methods, devices, and kits of the invention.

Figure 12:
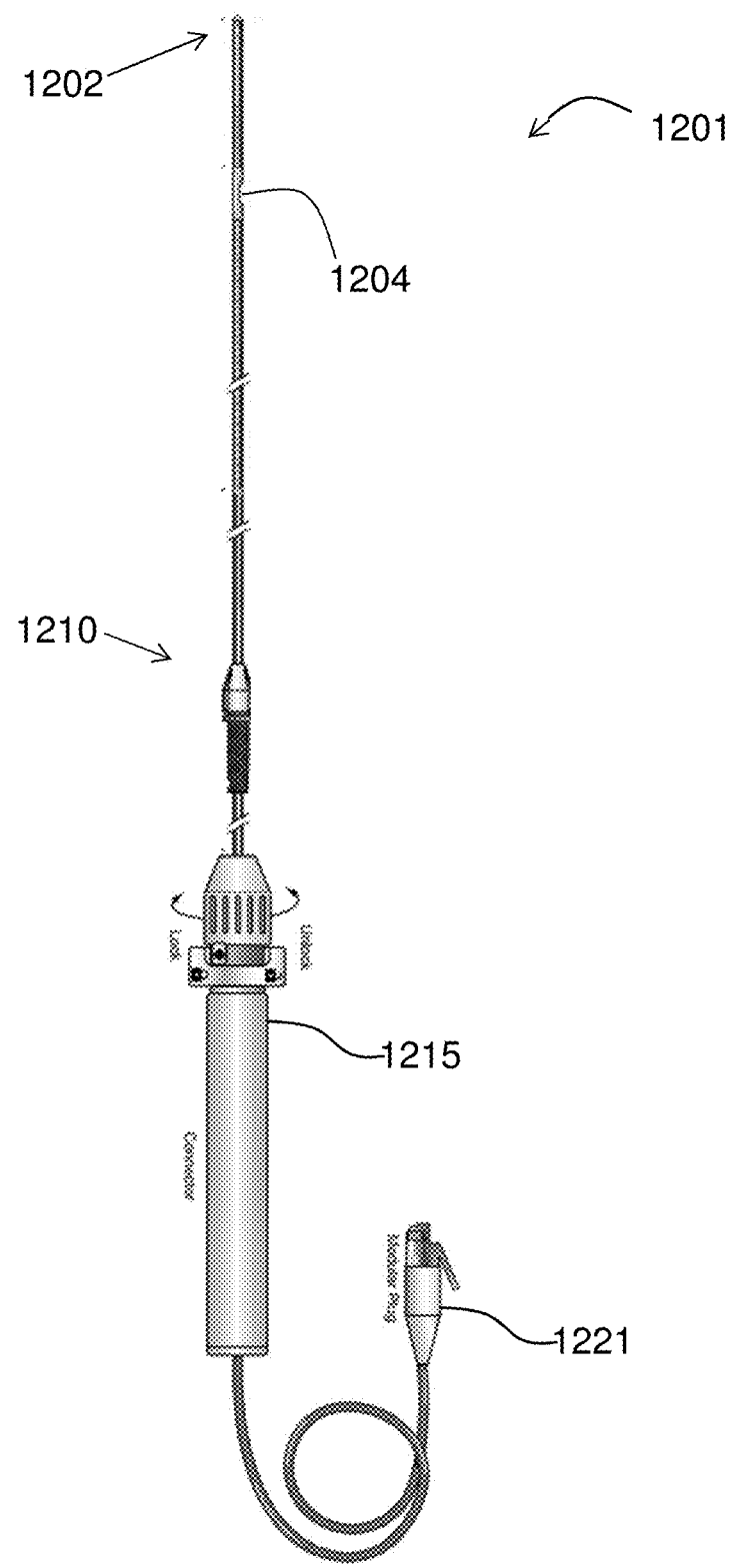
FIG. 12 presents a guidewire with a pressure sensor.

FIG. 12 illustrates a guidewire 1201 with a pressure sensor 1204. Guidewire 1201 generally defines an elongated body extending from a proximal end 1210 to a distal end 1202. Proximal end 1210 connects to connector housing 1215, which offers a modular plug 221 for connection to a computing device in systems of the invention.

A pressure sensor allows one to obtain pressure measurements within a body lumen. A particular benefit of pressure sensors is that pressure sensors allow one to measure of fractional flow reserve (FFR) in vessel, which is a comparison of the pressure within a vessel at positions on either side of the shunt. The level of FFR determines the patency of the shunt.

Pressure sensor 1204 can be mounted on the distal portion of a flexible elongate member. In certain embodiments, the pressure sensor is positioned distal to the compressible and bendable coil segment of the elongate member. This allows the pressure sensor to move away from the longitudinal axis and coil segment as bended. The pressure sensor can be formed of a crystal semiconductor material having a recess therein and forming a diaphragm bordered by a rim. A reinforcing member is bonded to the crystal and reinforces the rim of the crystal and has a cavity therein underlying the diaphragm and exposed to the diaphragm. A resistor having opposite ends is carried by the crystal and has a portion thereof overlying a portion of the diaphragm. Electrical conductor wires can be connected to opposite ends of the resistor and extend within the flexible elongate member to the proximal portion of the flexible elongate member. Additional details of suitable pressure sensors that may be used with devices of the invention are described in U.S. Pat. No. 6,106,476, which describes suitable methods for mounting the pressure sensor 1404 within a sensor housing. As discussed above, additionally or alternatively, a guidewire can include a flow sensor. In some embodiments, a guidewire is used that includes a flow sensor. A suitable product for guidewire 1201 is the PrimeWire PRESTIGE from Volcano Corporation. Preferably the guidewire includes of a flexible elongate element having proximal and distal ends and a diameter of 0.018" or less as disclosed in U.S. Pat. Nos. 5,125,137, 5,163,445, 5,174,295, 5,178,159, 5,226,421, 5,240,437 and 6,106,476, each incorporated by reference.

A guidewire of the invention may include a flexible elongate element having proximal and distal extremities, and can be formed of a suitable material such as stainless steel, Nitinol, polyimide, PEEK or other metallic or polymeric materials having an outside diameter for example of 0.018" or less and having a suitable wall thickness, such as, e.g., 0.001" to 0.002". This flexible elongate element is conventionally called a hypotube. In one embodiment, the hypotube may have a length of less than 120 cm, preferably about 50, 150, 70, or 80 cm. Typically, such a guide wire may further include a stainless steel core wire extending from the proximal extremity to the distal extremity of the flexible elongate element to provide the desired torsional properties to facilitate steering of the guide wire in the vessel and to provide strength to the guidewire and prevent kinking. The guidewire can have a diameter of about 0.014" (0.35 mm) and can include the functional instrumentation of the Doppler guide wire sold under the name FLOWIRE by Volcano Corporation, the pressure guidewire sold under the name PRIMEWIRE PRESTIGE by Volcano Corporation, or both.

Guidewire 1201 with a pressure sensor 1204 may be used to measure pressure and thus a pressure gradient may be measured. Depending on the pressure gradient measured between the portal vein and right atrium after stent or stent graft placement, a larger angioplasty balloon catheter may be used for stepwise decompression. Guidewire 1201 measures blood pressure after the procedure within the main portal vein. Once the value is stabilized and recorded, pressure sensor 1204 is moved to the hepatic vein or the suprahepatic inferior vena cava, and the blood pressure is again recorded. This can provide pressure values in the portal vein and hepatic vein before and after shunt placement to aid in evaluating the procedure.

Additionally or alternatively, blood flow velocity may be measured using a guidewire with a functional measurement sensor.

Figure 13:
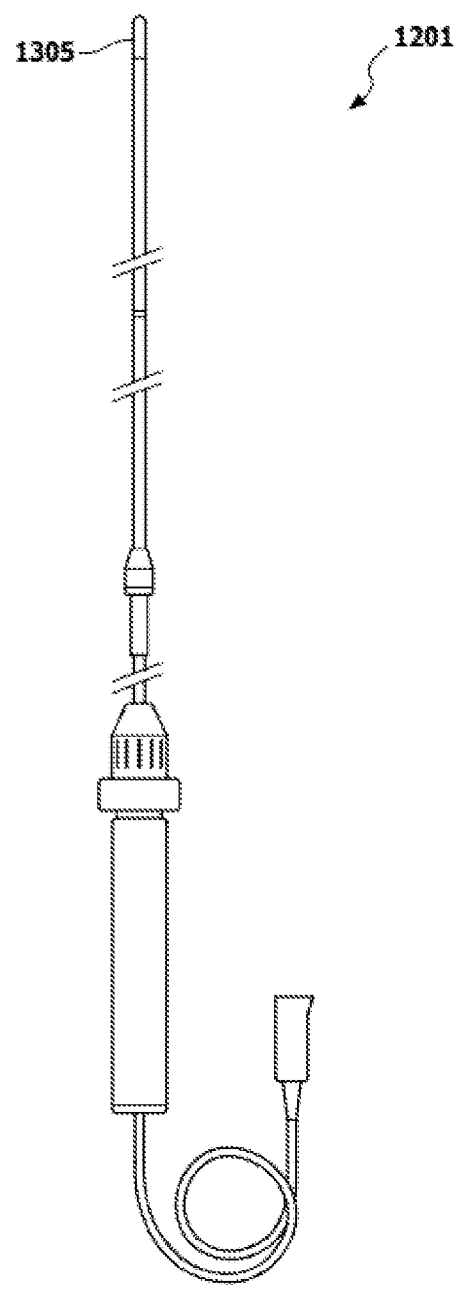
FIG. 13 illustrates a guidewire with a flow sensor.

FIG. 13 illustrates a guidewire 1201 with a flow sensor 1305. The flow sensor can be used to measure blood flow velocity within the vessel, which can be used to assess coronary flow reserve (CFR), or similar. The flow sensor can be, for example, an ultrasound transducer, a Doppler flow sensor or any other suitable flow sensor, disposed at or in close proximity to the distal tip of the guidewire. The ultrasound transducer may be any suitable transducer, and may be mounted in the distal end using any conventional method, including the manner described in U.S. Pat. Nos. 5,125,137, 6,551,250 and 5,873,835. A suitable product for guidewire 1201 with a flow sensor 1305 is the FLOWIRE from Volcano Corporation.

In a preferred embodiment, methods of the invention employ a guidewire that includes a device for measuring pressure and a device for measuring flow, i.e., a combination tip.

Figure 14:
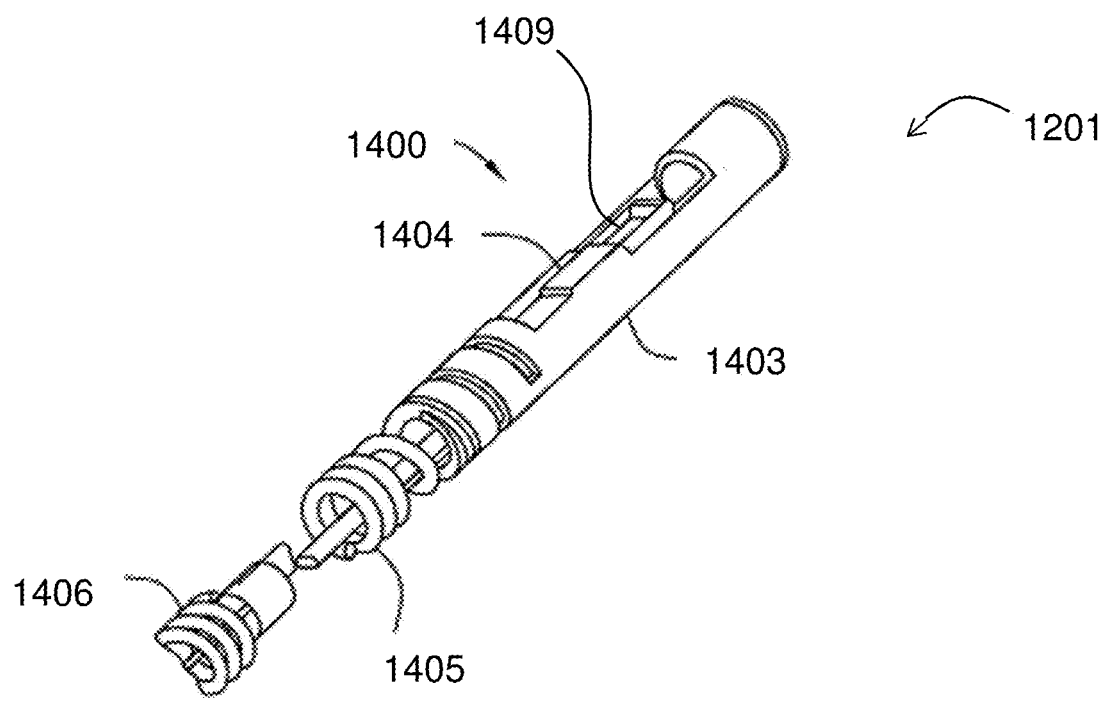
FIG. 14 shows a combination sensor tip of a guidewire.

FIG. 14 shows a combination sensor tip 1400 of a guidewire 1201 according to embodiments of the present invention. The combination sensor tip 1400 includes a pressure sensor 1404 within sensor housing 1403, and optionally includes a radiopaque tip coil 1405 distal to proximal coil 1406. Combination sensor tip includes an ultrasound transducer 1409 disposed therein. The ultrasound transducer 1409 may be any suitable transducer, and may be mounted in the distal end using any conventional method, including the manner described in U.S. Pat. No. 5,125,137, which is fully incorporated herein by reference. Conductors (not shown) may be secured to the front and rear sides of the ultrasound transducer 1409, and the conductors may extend interiorly to the proximal extremity of a guide wire.

The combination sensor tip 1400 also includes a pressure sensor 1404 in close proximity to the distal end 1202 of the combination sensor tip 1400. The pressure sensor 1404 may be of the type described above. The combination sensor tip 1400 is advantageous because by having both the ultrasound transducer 1409 and the pressure sensor 1404 near its distal end, the combination sensor tip 1400 is capable of being positioned distally beyond the shunt. Additionally, the combination sensor tip 1400 is able to take measurements from the ultrasound transducer 1409 and the pressure 104 at approximately the same location and approximately the same time. Constructions suitable for use with a guidewire of the invention are discussed in U.S. Pub. 2013/0030303 to Ahmed, the contents of which are incorporated by reference.

Figure 15:
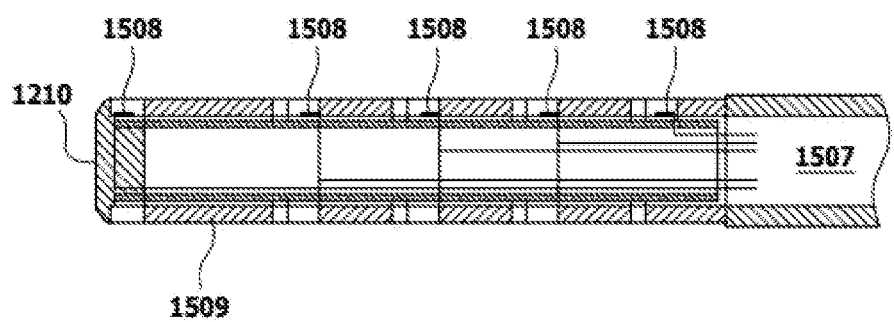
FIG. 15 shows fine wire conductors of a guide wire.

FIG. 15 shows fine wire conductors 1507 passing through the guide wire to conductive bands 1508 near the proximal end 1210 of the guide wire. Signals from the ultrasound transducer 1409 and the pressure sensor 1404 may be carried by conductors 1507. Usually three electrical connectors are necessary for a stand-alone pressure measurement guidewire and two electrical connectors are necessary for a stand-alone flow measurement guidewire. A guide wire incorporating the combination sensor tip 1400 of the present invention includes electrical conductors 1507 extending through the lumen of the guidewire and conductive bands 1508 on the proximal end of the guidewire. The conductive bands 1508 may be electrically isolated from each other by means of epoxy 1509. Alternatively, polyimide tubes may be used to isolate conductors from the conductive bands.

The electrical connection wires can include a conductive core made from a conductive material, such as copper, and an insulating coating, such as a polyimide, Fluoro-polymer, or other insulating material. The electrical connection wires extend from one or more sensors located on the distal end of the guidewire, run down the length of the guidewire, and connect to a connector housing at a proximal end.

Any suitable arrangement of the electrical connection wires through the length of the elongate member can be used. The arrangement of electrical connection wires provides for a stable connection from the proximal end to the distal end of the guidewire. Preferably, proximal end 1210 connects to connector housing 1215 as shown in FIG. 12. In certain embodiments, the electrical connector wires are joined together to form a male connector at a proximal end. The male connector mates with a female connector of the connector housing. The termination of the male connector can be performed by a metal deposition process as described in U.S. Pat. No. 6,210,339, incorporated herein by reference in its entirety. The deposited metal (or any conductive material) permanently adheres or couples to the exposed conductive wires at points where the polyimide layers were removed. After the masking material is removed, there are independent conductive stripes, each connected to a different respective electric wire. Because of the precision nature of the winding process as well as the masking and metal deposition processes, a male connector is made that is short in length, yet very reliable, in mating with a female connector and cable. Alternatively, conductive bands may be coupled to the exposed ends of the electric wires instead of the metallizing process.

The connector housing can be connected to an instrument, such as a computing device (e.g. a laptop, desktop, or tablet computer) or a physiology monitor, that converts the signals received by the sensors into pressure and velocity readings in systems of the invention.

As discussed above, methods and devices of the invention may include one or any combination of intravascular imaging sensor 505, pressure sensor 1204, flow sensor 1305, or combination sensor tip 1400. Data collected from such devices may be received at an imaging instrument, computer system, or both.

Figure 16:
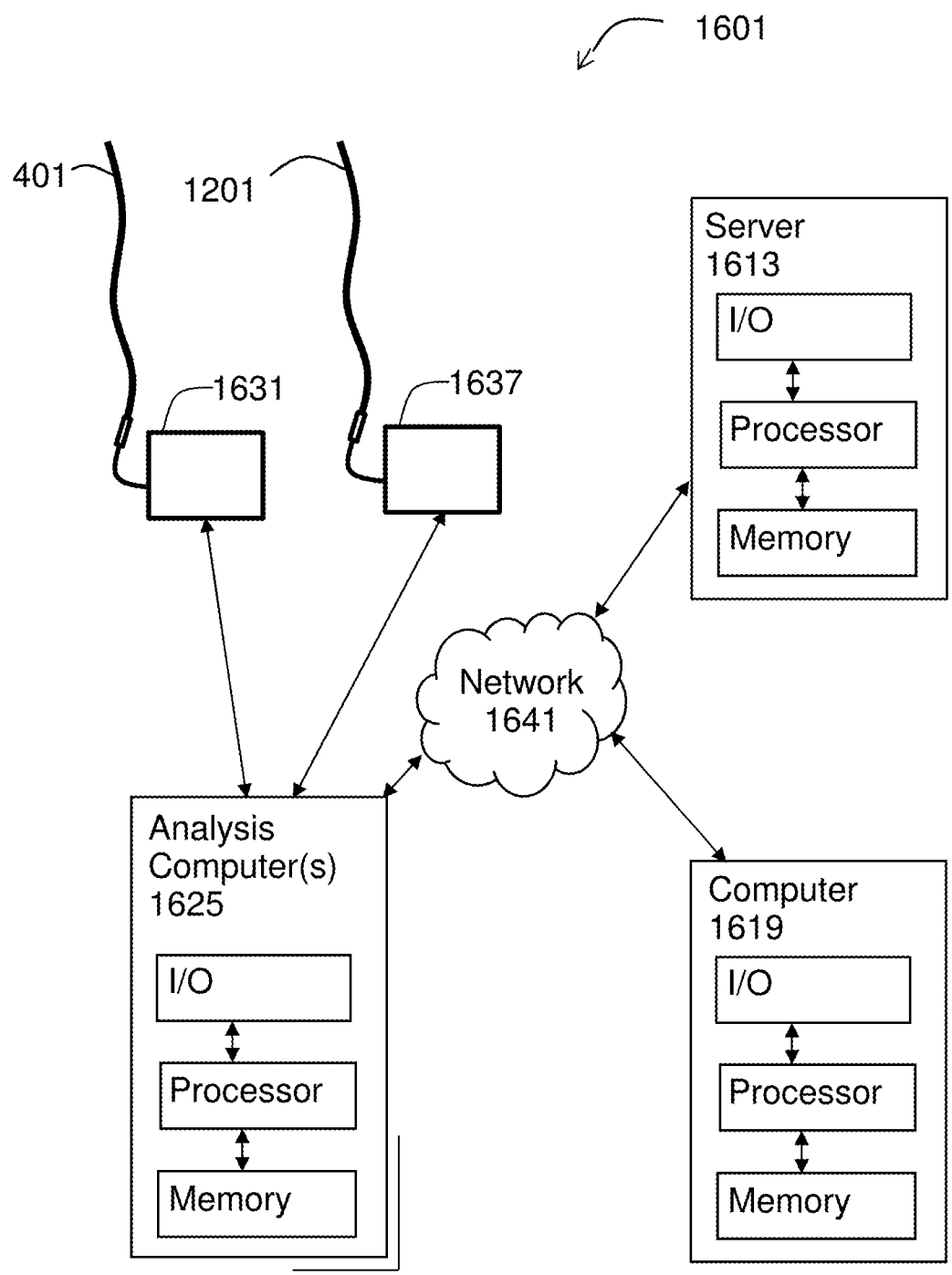
FIG. 16 illustrates a system of the invention.

FIG. 16 illustrates a system 1601 of the invention. System 1601 includes catheter 401 and intravascular imaging base station 1631 to receive intravascular imaging data from imaging device 505. Base station 1631 may include, for example, a field-programmable gate array to convert the raw incoming data into files for analysis by computer 1625. System 1601 optionally includes an instrumented guidewire 1201 operably coupled to a computer device 1625 via functional measurement base station 1637 (which can be integrated into base station 1631). Guidewire 1201 includes at least one sensor such as a pressure sensor or flow sensor as discussed above. Guidewire 1201 may include a plurality of sensor such as a pressure sensor and a flow sensor as discussed above. Computer 1625 can be a dedicated medical imaging instrument, a standard desktop, laptop, or tablet computer, or a combination thereof (e.g., a medical imaging instrument with a base station and a laptop or desktop computer attached to provide a workstation and interface for a physician.

In some embodiments, a user interacts with a visual interface (e.g., a monitor as I/P of computer 1625) to view images from the imaging system to see the portal vein in 3D and guide needle 501 thereto. For functional measurement guidewire 1201, electrical signals are relayed from the conductors via a mating connector (or contact housing as described herein with respect to a connector of the present invention) to base station 1637 that converts the signals into pressure and velocity readings that are displayed to the user. In addition algorithms such as Coronary Flow Reserve (CFR) or Fractional Flow Reserve (FFR) may be calculated.

System 1601 may include one or a plurality of computers. For example, system 1601 may include bed-side workstation computer 1625, a connected computer 1619 (e.g., in a control room), or both and system 1601 may additionally include a server computer 1613 for processing measurements. A computer in system 1601 such as computer 1625 or connected computer 1619 generally includes a processor coupled to memory and one or more input/output devices. Computer 1625 or 1619 may be provided by a desktop computer, laptop, tablet, mobile device, or purpose-built machine (such as a bed-side control station for a medical imaging system).

A processor generally refers to a computer microchip such as the processor sold under the trademark CORE I7 by Intel (Santa Clara, Calif.).

Memory generally includes one or more devices for random access, storage, or both. Preferably, memory includes a tangible, non-transitory computer readable medium, and may be provided by one or more of a solid state drive (SSD), a magnetic disc drive (aka, "a hard drive"), flash memory, an optical drive, others, or a combination thereof.

An I/O device may include one or more of a monitor, keyboard, mouse, touchscreen, Wi-Fi card, cell antenna, Ethernet port, USB port, light, accelerometer, speaker, microphone, drive for removable disc, others, or a combination thereof. Preferably, any combination of computer in system 1601 may communicate through the use of a network, which may include communication devices for internet communication, telephonic communication, others, or a combination thereof.

Other aspects of the invention include a device with one or more balloons or other elements for positioning, centering, or stabilizing the device.

Figures 17, 18:
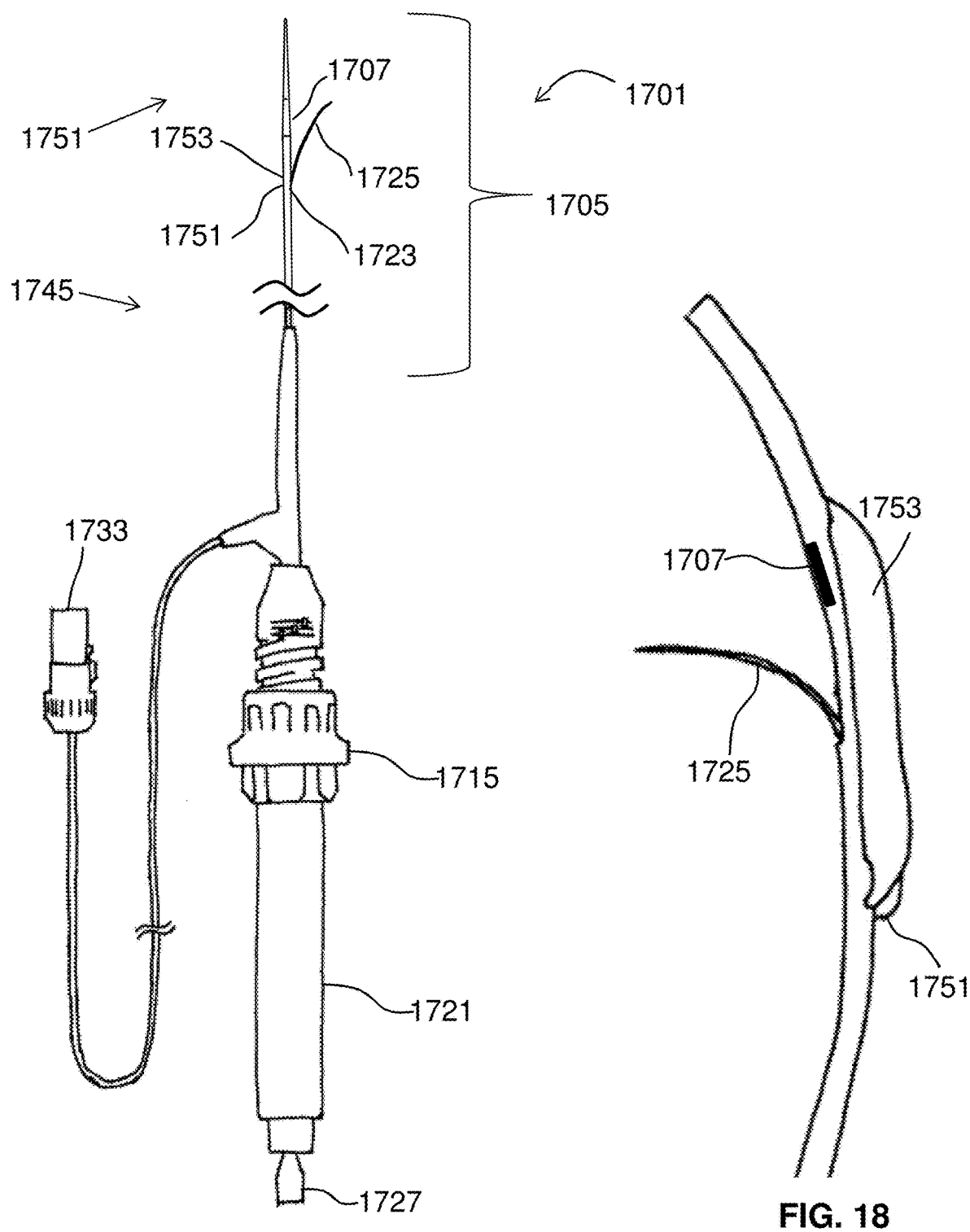
FIG. 17 depicts a shunt creation apparatus that uses a positioning mechanism.
FIG. 18 shows a device 1 with a first balloon and a second balloon inflated.

FIG. 17 depicts an apparatus 1701 for creating an intrahepatic portosystemic shunt. Apparatus 1701 may be used to create the access between the two vessels. Apparatus 1701 includes a catheter with an extended body 1705 having a distal portion 1751 and a proximal portion 1745. The catheter extends from handle 1721 and may include a needle deployment portion 1715 having needle depth markers and a locking needle stop ring. At the base of handle 1721 is an access port 1727 with openings to a needle guide wire lumen and one or more inflation lumens. Connected to and extending from proximal portion 1745 is a connector 1733 for connection to an imaging instrument. Needle 1725 can be seen extended from needle exit port 1723. Apparatus 1701 further includes a first balloon 1751 and a second balloon 1753 disposed FIG. 17 shows needle 1725 extending from an exit port 1723 on a side of distal portion 1751 of catheter 1701. Device 1701 includes intravascular imaging sensor 1707—which may include an ultrasound transducer—e.g., disposed just distal to the exit port 1723, although it can be located in other places. Needle 1725 preferably provides a lateral reach (LR) of at least 1 cm. This allows needle 1725 to reach portal vein 145. First balloon 1751 and a second balloon 1753 provide beneficial stabilizing functionality to aid in effective creation of an intrahepatic shunt.

FIG. 18 shows device 1701 with first balloon 1751 and a second balloon 1753 inflated and needle 1725 deployed. Device 1701 may have the balloons inflated and the needle extended when deployed within hepatic vein 149. Imaging sensor 1707 can view portal vein, aiding a practitioner in creating a shunt. In certain embodiments, sensor 1707 includes one or more IVUS transducers for taking intravascular images via ultrasound.

Figure 19:
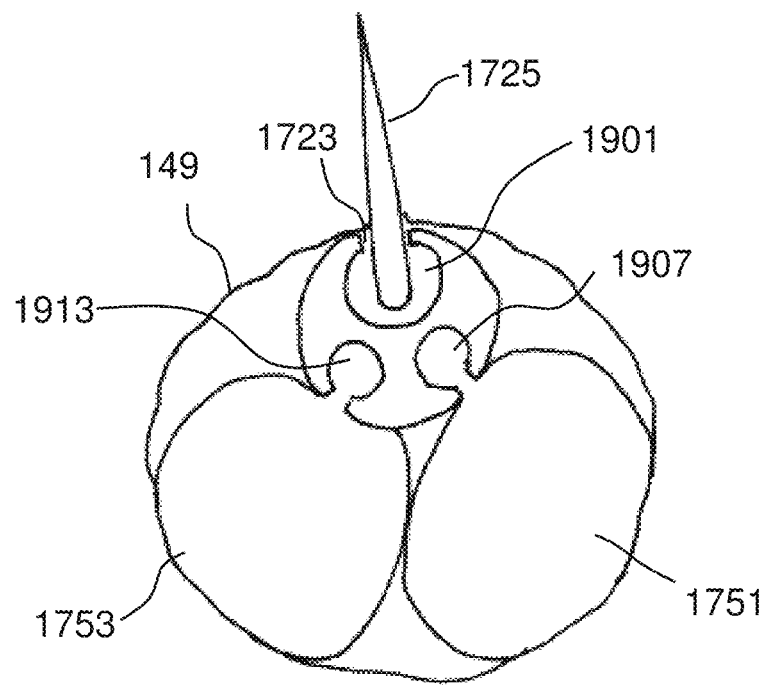
FIG. 19 gives a cross-section view of a device with a multi-balloon positioning mechanism.

FIG. 19 gives a cross-section view of device 1701 showing a first inflation lumen 1907 for inflating first balloon 1751, second inflation lumen 1913 for inflating second balloon 1753, and needle lumen 1901, which lumens extend through the catheter of device 1701. The arrangement of first balloon 1751 and a second balloon 1753 as depicted in FIGS. 18 & 19 provides a useful tool for aiding in a TIPS procedure. The balloons can be used to brace the device 1701 against the wall of the hepatic vein 149. Needle 1725 is extended from apparatus 1701 and used to cross the tissue between portal vein 145 and hepatic vein 149, thus creating a shunt. The needle 1725 is extended from catheter device 1701 and used to puncture the liver from a central portion of the hepatic vein 149 while first balloon 1751 and a second balloon 1753 brace the device 1701 therein.

Figure 20:
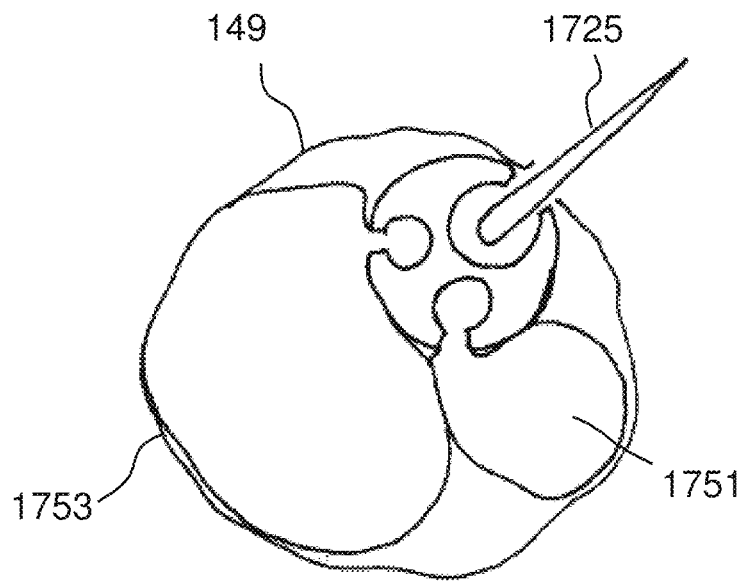
FIG. 20 illustrates use of the positioning device.

One benefit of including a first balloon 1751 and a second balloon 1753 as depicted in FIG. 19 and FIG. 20 is that a practitioner may modulate the relative inflation of the two balloons to adjust the positioning of the needle 1725. Using FIGS. 19 and 20 for reference, if the inflation of first balloon 1751 is decreased by, for example, 20% while the inflation of the second balloon is increased by 20%, the change in inflation of the two balloons will bias the orientation of the needle 1725 in a clockwise direction (according to the depiction of FIGS. 19 and 20). It will be appreciated that the relative inflation of the two balloons can be controlled to any desired amount to bias the needle in either direction or to give additional support to the needle on one side versus the other where anatomical context demands.

Thus it can be seen that in some embodiments, the invention provides a method of creating an intrahepatic portosystemic shunt that includes directing a catheter 1701 down a jugular vein and into a hepatic vein 149 of a patient and operating an imaging device 1707 disposed on the catheter from within the hepatic vein to obtain an image of a portal vein of the patient. A first balloon 1751 disposed on catheter 1701 in a location substantially opposed to a needle exit port 1723 may be inflated to aid in bracing the needle 1725 for penetration of the hepatic tissue or to orient the needle 1725. A second balloon 1753 disposed on catheter 1701 in a location substantially opposed to a needle exit port 1723 and the first balloon 1751 may be inflated to aid in bracing the needle 1725 for penetration of the hepatic tissue or to orient the needle 1725. The method further includes extending the needle 1725 out from the needle lumen 1901 within the catheter 1701 to create a shunt defining a passageway through which blood can flow from the portal vein to the hepatic vein. In a preferred embodiment, the first balloon 1751 and the second balloon 1753 extend along the body of catheter 1701 substantially parallel to one another and spaced apart from one another and each spaced apart from the needle exit port 1723 (i.e., all spaced about equidistant apart along a circumference around the catheter 1701). The practitioner may view an image of the portal vein while adjusting the orientation of the needle 1725 by adjusting the relative inflation of the balloons. The invention further includes methods and devices that use other features and combinations of features discussed herein.

In certain aspects and embodiments, the invention provides a kit for a TIPS procedure. The kit includes a guidewire 1201 with a functional measurement sensor and a catheter apparatus 401 having a needle 501 disposed therein. Catheter 401 includes an intravascular imaging device such as an IVUS transducer on a distal portion of the extended body with a needle exit port also on the distal portion of the extended body. Needle 501 is disposed within a lumen in the catheter and configured to be pushed out of the exit port and extend away from a side of the extended body by a distance of at least one centimeter. Needle 501 can be removed from catheter 401 and guidewire 1201 may be advanced through catheter 401 to aid in delivery of a stent 1109. A pressure sensor 1204 (or optionally a flow sensor 1305 or combination sensor tip 1400) may be used to measure pressure, flow velocity, or both in shunt 607. The kit is well suited for creation of portosystemic shunts as discussed herein. Aspects of the invention may provide a kit that includes catheter 401 and stent 1109. Useful background may be found in U.S. Pat. No. 7,729,738 to Flaherty (e.g., columns 17-18); U.S. Pat. No. 8,632,468 to Glossop; and U.S. Pat. No. 8,346,344 to Pfister, the contents of each of which are incorporated by reference for all purposes.

Additional features that may be included in a device of the invention include one or more of a centering mechanism, an extended or beveled needle, an aspiration catheter, a lumen for delivery of an agent, virtual histology functionality provided by a computer system, virtual biopsy functionality, an ablation mechanism on a catheter, devices for embolization of endoleaks, or any combination thereof. Devices and methods of the invention may find use in other procedures (e.g., portal vein thrombosis, portal vein hypertension).

A centering mechanism may include a balloon, struts, a trough, or other mechanism to stabilize the device so that it can accurately image and access the second vessel. Centering mechanisms that may be suitable for modification use with the invention are discussed in Volcano Corporation's U.S. patent application Ser. No. 14/201,070, filed Mar. 7, 2014.

Needle 501 is depicted in FIG. 9 has having beveled tip 901, shown in greater detail in FIG. 10. It is noted that tip 901 may be extended, beveled, or elongated, i.e., to an extent not depicted in FIG. 10, to increase lateral reach (e.g., to LR≥2 cm or 2.5 cm).

Device 401 may include a lumen to provide an aspiration catheter or needle 501 may include a lumen to serve a lytic delivery/aspiration catheter for thrombosis in the liver. Thus device 401 or needle 501 could be used to deliver an agent such as a lytic agent.

System 1601 may include virtual histology functionality provided by a computer system that receives data from intravascular imaging sensor 505, pressure sensor 1204, flow sensor 1305, or combination sensor tip 1400. A window in needle may be used to determine tissue coefficient. System 1601 may provide virtual biopsy functionality (e.g., for cancer detection). Virtual histology is discussed in Volcano Corporation's patent application Ser. No. 14/106,260, filed Dec. 13, 2013, and see also U.S. Pub. 2014/0100440

Device 401 may include an ablation mechanism on a catheter. For example, a distal end of the catheter may include an electrode coupled to an RF generator. The generator delivers RF energy to the electrode to ablate occluding material in the vessel. The electrode may have a variety of tip shapes including concave, roughened, or expandable configurations, depending on the size of the vessel and composition of the occluding material. See U.S. Pat. No. 6,638,222 to Chandrasekaran; U.S. Pat. No. 5,385,148 to Jackson; and U.S. Pat. No. 8,480,593 to Magnin.

As discussed herein, the invention provides methods, devices, and kits that may be used for treatment of cirrhosis or conditions such as portal hypertension or variceal bleeding. Additional information may be found in Perz et al., 2006, The contributions of hepatitis B virus and hepatitis C virus infections to cirrhosis and primary liver cancer worldwide, J. Hepatol 45(4):529-38; Yin et al., 2013, the surgical treatment for portal hypertension: a systematic review and meta-analysis, ISRN Gastroenterology article ID 464053; and Jalan et al., 2000, TIPSS 10 years on, Gut 46:578-581.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. An apparatus for creating an intrahepatic portosystemic shunt, the apparatus comprising:
 a catheter with an extended body configured for insertion down a jugular vein into a hepatic vein of a patient;
 an intravascular imaging device on a distal portion of the extended body;
 a needle exit port on the distal portion of the extended body, the needle exit port comprising an opening; and
 a needle comprising an extended portion and a distal portion constructed of a shape-memory metal, whereupon being in a lumen of the catheter, the distal portion of the needle is configured to maintain the shape of the catheter, and whereupon extending out of the opening of the needle exit port and away from a side of the extended body, the distal portion of the needle is configured to assume a curved shape, wherein the curved shape comprises (i) an angle between 55 degrees and 79 degrees measured between a distal tip of the distal portion and the extended portion of the needle and (ii) a lateral reach between 1 cm and 2.5 cm, wherein the lateral reach is a distance from the extended portion of the needle to the distal tip in a direction perpendicular to a longitudinal axis of the extended portion of the needle; and
 a pressure sensor disposed on the distal portion of the needle.

2. The apparatus of claim 1, wherein the pressure sensor is disposed on the distal portion of the needle a distance from the distal tip, wherein the distance is less than 50% of the lateral reach.

3. The apparatus of claim 2, wherein the needle comprises a shape memory metal that assumes a curved shape as the needle exits the nonadjustable needle exit port.

4. The apparatus of claim 3, wherein the needle comprises a lumen extending therethrough, the lumen dimensioned to receive a guidewire.

5. The apparatus of claim 3, wherein the intravascular imaging device comprises an ultrasound transducer.

6. The apparatus of claim 5, wherein the needle is dimensioned to extend from the non-adjustable needle exit port away from the side of the catheter body through tissue and into a portal vein.

7. The apparatus of claim 6, wherein the distal tip is a sharp tip configured to pierce through the tissue between the hepatic vein and the portal vein thereby creating a portosystemic shunt.

8. The apparatus of claim 7, wherein the ultrasound transducer is operable to produce an image of the portal vein when within the hepatic vein.

9. The apparatus of claim 8, wherein a proximal end of the catheter is attached to an imaging system comprising a processor and a display, and wherein the image produced by the ultrasound transducer is viewable on the display.

10. The apparatus of claim 1, further comprising a positioning mechanism operable to bias a portion of the extended body towards a side of the hepatic vein.

11. The apparatus of claim 10, wherein the positioning mechanism comprises a first balloon and a second balloon disposed in parallel to one another along a length of the extended body.

12. The apparatus of claim 1, wherein the needle comprises a lumen for delivering a treatment agent to tissue.

13. The apparatus of claim 1, wherein the angle is at least 65 degrees.

14. The apparatus of claim 1, wherein the distal tip is a beveled tip.

15. The apparatus of claim 14, wherein the beveled tip defines the angle with the extended body, and the angle is at least 65 degrees.

16. An apparatus for creating an intrahepatic portosystemic shunt, the apparatus comprising:
 a catheter with an extended body configured for insertion down a jugular vein into a hepatic vein of a patient, a distal portion of the extended body having a first side and a second side opposing the first side;
 an intravascular imaging device on the distal portion of the extended body;
 a needle exit port on the first side of the distal portion of the extended body;
 a needle disposed within a lumen in the catheter and configured to be pushed out of the exit port and extend away from the first side of the distal portion of the extended body; and
 a first balloon and a second balloon disposed on the second side of the distal portion of the extended body and in parallel to one another along a length of the extended body and partially spaced apart from one another along a circumference of the extended body, wherein inflation of the first balloon and the second balloon biases a portion of the extended body towards a side of the hepatic vein.

17. The apparatus of claim 16, wherein the needle comprises a distal tip, wherein the distal tip has a lateral reach of at least 1 cm, wherein the lateral reach is a perpendicular distance from the extended body to the distal tip.

18. The apparatus of claim 17, wherein the needle comprises a shape memory material that assumes a curved shape as the needle exits the exit port.

19. The apparatus of claim 18, further comprising a pressure sensor disposed on the needle a distance from a distal tip of the needle, wherein the distance is less than 50% of the lateral reach.

20. The apparatus of claim 16, wherein the intravascular imaging device comprises an ultrasound transducer operable to produce an image of a portal vein when within the hepatic vein.

* * * * *